(12) United States Patent
Romoli et al.

(10) Patent No.: US 11,439,713 B2
(45) Date of Patent: Sep. 13, 2022

(54) METHOD FOR CREATING A RENAL INJURY MODEL TO SCREEN MOLECULES FOR THE TREATMENT OF RENAL INJURY

(71) Applicant: BAYER AKTIENGESELLSCHAFT, Leverkusen (DE)

(72) Inventors: Simone Romoli, Great Shelford (GB); Tobias Bauch, Wuppertal (DE); Karoline Dröbner, Velbert (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 1 day.

(21) Appl. No.: 16/493,613

(22) PCT Filed: Mar. 2, 2018

(86) PCT No.: PCT/EP2018/055195
§ 371 (c)(1),
(2) Date: Sep. 12, 2019

(87) PCT Pub. No.: WO2018/166813
PCT Pub. Date: Sep. 20, 2018

(65) Prior Publication Data
US 2020/0000939 A1 Jan. 2, 2020

(30) Foreign Application Priority Data

Mar. 13, 2017 (EP) .................................... 17160591
Apr. 5, 2017 (EP) .................................... 17165101

(51) Int. Cl.
| A61K 49/00 | (2006.01) |
| G01N 33/50 | (2006.01) |
| G01N 33/68 | (2006.01) |
| G01N 33/70 | (2006.01) |

(52) U.S. Cl.
CPC ..... *A61K 49/0008* (2013.01); *G01N 33/5008* (2013.01); *G01N 33/6827* (2013.01); *G01N 33/70* (2013.01); *G01N 2500/00* (2013.01); *G01N 2800/347* (2013.01)

(58) Field of Classification Search
None
See application file for complete search history.

(56) References Cited

FOREIGN PATENT DOCUMENTS

EP 2944326 11/2015

OTHER PUBLICATIONS

Emans et al. Exogenous and endogenous angiotensin-II decrease renal cortical oxygen tension in conscious rats by limiting renal blood flow. 2016 J. Physiol. 594: 6287-6300. Epub Aug. 18, 2016. (Year: 2016).*

Axelsson J et al., "Rapid, dynamic changes in glomerular permeability to macromolecules during systemic angiotensin II (ANG II) infusion in rats." American Journal of Physiology-Renal Physiology 303.6 (2012): F790-F799.
Campas C et al, Drugs Fut., 2009.
Cérvenka et al, "Angiotensin II-induced hypertension in bradykinin B2 receptor knockout mice." Hypertension 37.3 (2001): 967-973.
Eckel J et al, "TRPC6 enhances angiotensin II-induced albuminuria." Journal of the American Society of Nephrology 22.3 (2011): 526-535.
Emmanuel A et al: "Snakebite-induced acute renal failure: An experimental model", American Journal of Tropical Medicine and Hygiene, vol. 48, No. 1,1993, pp. 82-88.
Gil et al, "Heparanase is essential for the development of diabetic nephropathy in mice." Diabetes 61.1 (2012): 208-216.
Gunal M Y et al: "Pleiotropic and Renoprotective Effects of Erythropoietin Beta on Experimental Diabetic Nephropathy Model", Nephron Apr. 1, 2016 S. Karger AG CHE, vol. 132, No. 4, Apr. 1, 2016 (Apr. 1, 2016), pp. 292-300.
Jeansson M et al, "Glomerular size and charge selectivity in the mouse after exposure to glucosaminoglycan-degrading enzymes." Journal of the American Society of Nephrology 14.7 (2003): 1756-1765.
Kang PM et al, "Angiotensin II receptor antagonists: a new approach to blockade of the renin-angiotensin system." American heart journal 127.5 (1994): 1388-1401.
Masola et al., "Heparanase: a potential new factor involved in the renal epithelial mesenchymal transition (EMT) induced by ischemia/reperfusion (I/R) injury." PloS one 11.7 (2016): e0160074.
McKenzie et al., "Heparanase: a target for drug discovery in cancer and inflammation." British journal of pharmacology 151.1 (2007): 1-14.
Quesada, A. et al: "Urinary 1-19 Aminopeptidase Activities as Early and Predictive Biomarkers of Renal Dysfunction in Cisplatin-Treated Rats", PLOS ONE, vol. 7, No. 7, Jul. 5, 2012.
Rippe C et al, "Size and charge selectivity of the glomerular filter in early experimental diabetes in rats." American Journal of Physiology—Renal Physiology 293.5 (2007): F1533-F1538.
Shibasaki T et al: "Characteristics of cadmium-induced nephrotoxicity in Syrian hamsters", Japanese Journal of Nephrology—Nihon Jinzo Gakkaishi, Nihon Jinzo Gakkai, Tokyo, JP, vol. 35, No. 8, Jul. 31, 1993 (Jul. 31, 1993), pp. 913-917, XP009504305.

(Continued)

*Primary Examiner* — Jennifer Lamberski
(74) *Attorney, Agent, or Firm* — Quarles & Brady LLP

(57) ABSTRACT

The present invention is related to short-term renal injury models and methods for creating these models. The models and methods can be used for identifying, testing or characterizing candidate molecules with respect to their suitability to treat renal injury. The methods comprise a step of inducing, in a test subject, renal injury by administering subcutaneously a bolus of a renal injury inducer, in a dosage sufficiently high to induce renal injury. Different types of readout for renal injury are provided such as albumin creatinine ratio (ACR) determined in a urine sample taken from the subject, or the development of transcutaneous fluorescence after injection of a fluorescent molecule. Based on the readout the degree of renal injury and/or alteration of GFR can be determined.

10 Claims, 9 Drawing Sheets

(56) References Cited

OTHER PUBLICATIONS

Sica Da et al, "Clinical pharmacokinetics of losartan." Clinical pharmacokinetics 44.8 (2005): 797-814.
Chin, S.Y et al., "Renoprotective effects of nitric oxide in angiotensin II-induced hypertension in the rat." American Journal of Physiology-Renal Physiology 274.5 (1998): F876-F882.
Timmermans P, "Angiotensin II receptors and angiotensin II receptor antagonists." Pharmacological reviews 45.2 (1993): 205-251.
Van Den Hoven et al, "Heparanase in glomerular diseases." Kidney international 72.5 (2007): 543-548.
Van Den Hoven et al, "Reduction of anionic sites in the glomerular basement membrane by heparanase does not ad to proteinuria." Kidney international 73.3 (2008): 278-287.

* cited by examiner

▶ AngII i.v. bolus + s.c. bolus

▶ p.o. treatment   T=0h                                              T=+4h 4h urinary collection for ACR Groups all p.o. Application before AngII injury induction
1. Control NaCl i.v. + s.c.
2. AngII 5µg i.v. + 5µg s.c.
3. AngII 8µg i.v. + 8µg s.c.
4. AngII 10µg i.v. + 10µg s.c.
5. AngII 10µg i.v. + 10µg s.c. + 30mg/kg Losartan

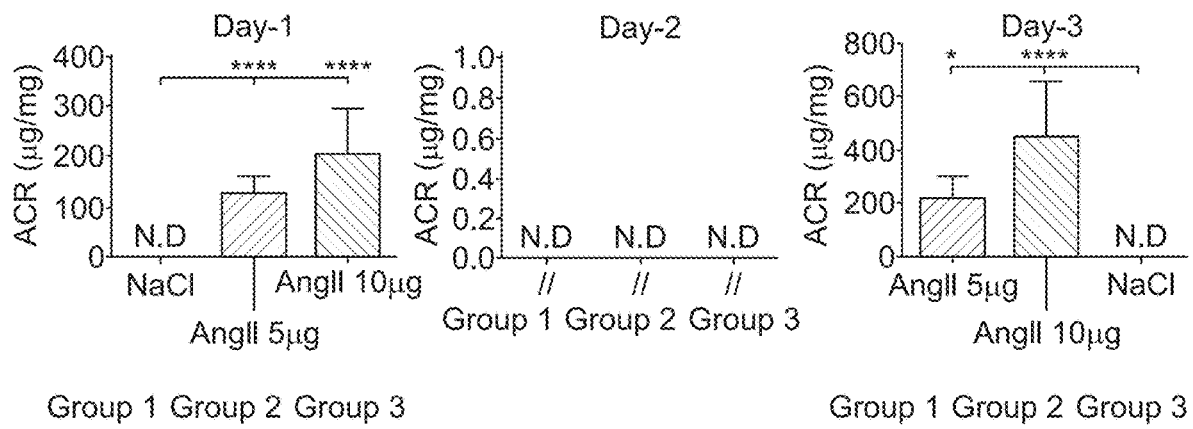

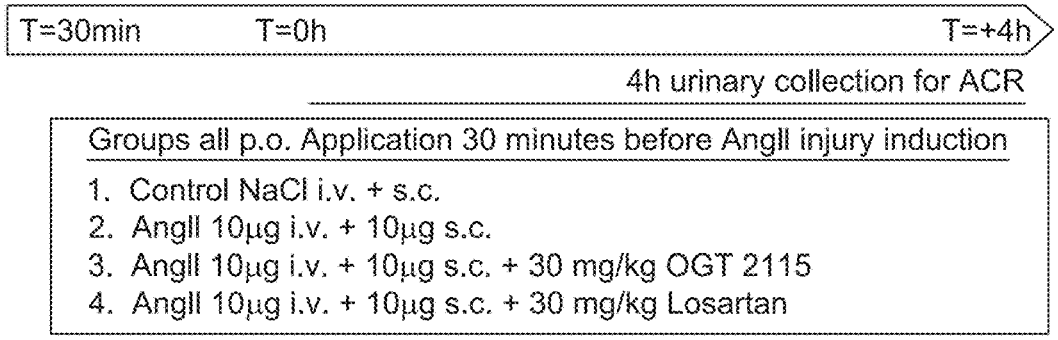
FIG. 9
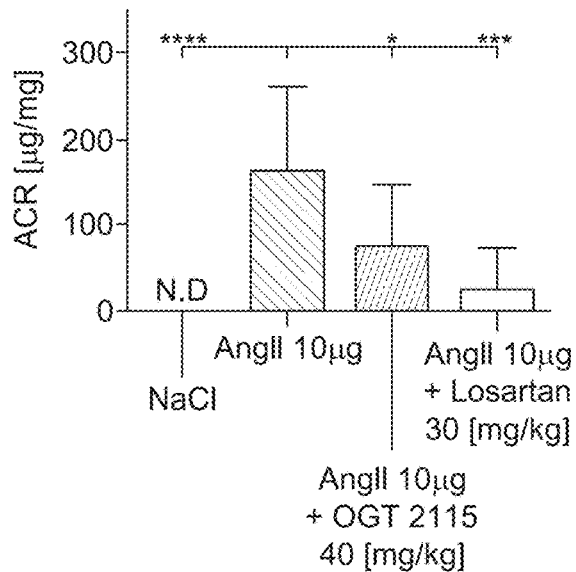
FIG. 10
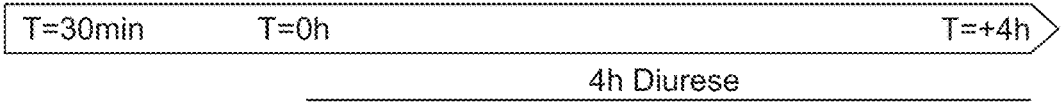
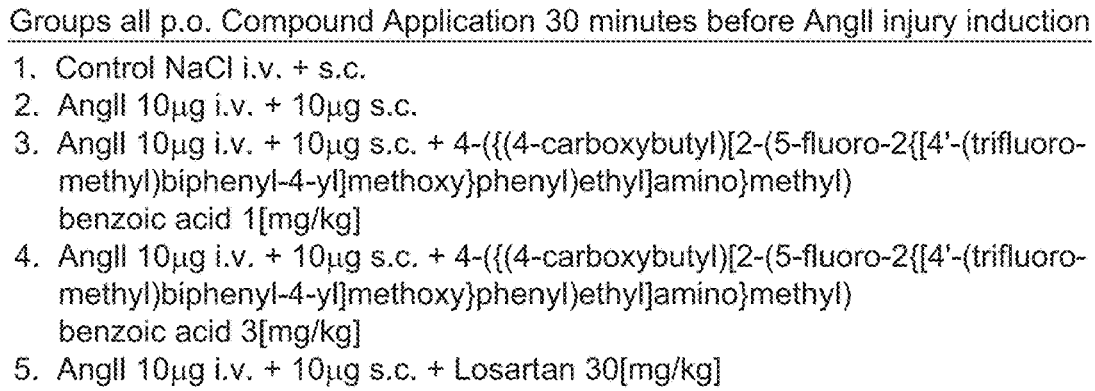
FIG. 11

METHOD FOR CREATING A RENAL INJURY MODEL TO SCREEN MOLECULES FOR THE TREATMENT OF RENAL INJURY

CROSS REFERENCE TO RELATED APPLICATIONS

This application is the U.S. national stage entry under 35 U.S.C. 371 of PCT/EP2018/055195, filed Mar. 2, 2018, which is hereby incorporated by reference herein, which claims benefit of priority to European Patent Application Nos. 17160591.8, filed Mar. 13, 2017, and 17165101.1, filed Apr. 5, 2017.

FIELD OF THE DISCLOSURE

The present invention is related to short-term renal injury models and methods for creating these models. The models and methods can be used for identifying, testing or characterizing candidate molecules with respect to their suitability to treat renal injury. The methods comprise a step of inducing, in a test subject, renal injury by administering subcutaneously and/or intravenously a bolus of a renal injury inducer, in a dosage sufficiently high to induce renal injury. Different types of readout for renal injury are provided such as albumin creatinine ratio (ACR) determined in a urine sample taken from the subject, or the development of transcutaneous fluorescence after injection of a fluorescent molecule. Based on the readout the degree of renal injury and/or alteration of GFR can be determined.

BACKGROUND

Chronic kidney disease (CKD) is characterized by the gradual loss of kidney function over a period of time. Known causes of CKD comprise diabetes, high blood pressure, glomerulonephritis, and polycystic kidney disease. Glomerulonephritis (GN) or glomerular nephritis refers to several kidney diseases, some of them being characterized by inflammation of the glomeruli or of the small blood vessels in the kidneys. Existing CKD classification system(s) can assist in predicting outcomes such as kidney disease progression and cardiovascular disease. They are furthermore applied to decide on therapeutic interventions in earlier stages to slow down disease progression, to improve quality of life and survival, or to reduce complications. These complications may for example relate to a decreased glomerular filtration rate (GFR).

Biomarkers such as albuminuria may precede kidney function decline and show strong correlations with disease progression and outcomes. Measured as ACR, albuminuria is the most sensitive indirect marker of CKD progression or glomerular filtration barrier (GFB) diseases in clinical practice. In clinical drug trials ACR has been used as surrogate endpoint. In humans, an ACR≤10 mg/g (≤1 mg/mmol) is considered normal, an ACR 10-30 mg/g (1-3 mg/mmol) is considered high normal and an ACR≥2200 mg/g (≥220 mg/mmol) is considered nephrotic range.

While there is a need for further drug development in the field of CKD and related diseases, identification, optimization and characterization of compounds with medical potential remains a challenge. In vivo kidney model systems are one option to identify or characterize substances with a potential effect in kidney related diseases Animal models of renal disease have provided valuable insights into the pathogenesis of acute and chronic kidney disease.

For these methods, the renal injury can be induced by a variety of methods. Surgical manipulations may reproduce the injury that causes renal disease (e.g. ureteric obstruction) or reproduce the consequences of renal injury (e.g. renal ischaemia, reduction in renal mass) Animal models based on surgical manipulations are technically demanding and not reversible. Technically challenging genetically engineered animal models are a further option for the induction of renal injury, but are characterized by high costs. Chemical induction of renal injury is a further option for the development of a renal model system. The group of chemical models can also comprise immunological models, where an antibody (e.g. anti-GBM antibodies) or sera are administered to induce the renal injury.

Typical methods for assessing GFR in small laboratory animals, as required for example in kidney disease models, nephrotoxicity studies or the characterization of genetically modified animals, are cumbersome, invasive and/or time consuming, due to required multiple blood and/or urine sampling and subsequent sample analysis. Common kidney in vivo models with albuminuria as a relevant readout parameter are likewise complicated invasive chronic models, with a typical duration of several weeks. These obstacles make the drug screening process challenging and susceptible to complications. Early direct evidence of GFB injury is only accessible with a glomerular histological end stage study or kidney biopsies, in humans as well in experimental nephrological animal models.

According to prior art renal nephrotic models, the renal injury is induced via a constant femoral vein infusion of human angiotensin peptide II (AngII). A brief description of such an approach is disclosed e.g. in Jeansson M et al, Journal of the American Society of Nephrology, 14(7), 2003, p. 1756-1765, Rippe C et al, American Journal Renal Physiology, 293(5), 2007, p. 1533-8, and Axelsson J et al., American Journal of Physiology—Renal Physiology, 303 (6), 2012, p. F790-F799, where the authors are exploring the filtration capability of the glomeruli, a renal sub unit responsible for blood filtration and production of the pre-urine in the inner glomerular space. In brief, following the cannulation of the left ureter, experiments start with an initial rest period of 20 min. After the rest period, sampling of urine and plasma for Ficoll-sieving measurements is performed during a 5-min control period for baseline determination, before the start of the infusion of AngII. AngII is given as an injury inducer by continuous infusion throughout the experiment. The integrity of the glomerular basement membrane (GBM) is investigated using a mixture of polymers with different molecular density. Ficoll-70 kDa and 400 kDa are used as readout parameters in the final urine output. When the GBM integrity is lost during a glomerular injury the amount and quality of the Ficoll mixture ratio can change with linear progression of GBM damage. In the absence of injury, the urine output does not contain the polymer, due to the GBMs capability to stop proteins with a specific molecular weight of 60 to 70 kDa. For sieving of FITC-Ficoll, a mixture of FITC-Ficoll-70 and FITC-Ficoll-400 was used in a 1:24 relationship together with FITC-inulin. The bolus dose was followed by constant infusion of 10 ml·kg$^{-1}$·h$^{-1}$ (FITC-Ficoll-70, 20 µg/ml; FITC-Ficoll-400, 0.48 mg/ml; FITC-inulin, 0.5 mg/ml; and $^{51}$Cr-EDTA, 0.3 MBq/ml) for at least 20 min before sieving measurements, after which urine from the left kidney was collected for 5 min, with a midpoint (2.5 min) plasma sample collected. Plasma and urine samples were assessed for FITC-Ficoll concentrations on a high-performance size exclusion chromatography (HPSEC) system.

The methodology described has several critical points: the necessity of ureter cannulation for urine sampling, femoral vein access for blood sampling as well as constant fluid infusion and AngII administration complicate the method. Handling of radioactive compounds such as $^{51}$Cr-EDTA for GFR assessment requires complicated and specific competences for radioactive-good practice guidelines, necessitating appropriate user-trainings and security clearances. In addition, procedures for handling of radioactive waste and samples are laborious in itself. Moreover, laboratory animals are anesthetized for the experimental procedure. The anesthesia induces a significant alteration of the GFR. In addition to these issues, the complex methodology has a high expenditure of time and a limited output, which is not in line with the needs of high throughput drug discovery.

So Yeon Chin et al. (American Journal of Physiology, 274(5 Pt 2), 1998, p. F876-82) describe an AngII infusion rat model, where synthetic AngII is delivered continuously at a rate of 65 ng/min via osmotic minipumps implanted at the dorsum of the neck. The AngII is infused into the interstitium to allow slow absorption into the circulation. A sham operation is performed on the normotensive control rats. After recovery, renal clearance experiments are performed 13 days after the implantation of minipumps or sham operation to assess renal hemodynamics. In 2001, Cervenka et al (Hypertension, 37(3), 2001, p. 967-973) transferred the described long term AngII-osmotic pump model from rat into mouse.

Eckel et al. (Journal of the American Society of Nephrology, 22(3), 2011, p. 526-535) describe a long term osmotic pump AngII infusion mouse model to study renal disease, wherein renal injury is induced by 28-day infusion of AngII at a dose of 1000 ng/kg/min using primed osmotic minipumps. The pumps were implanted subcutaneously in the dorsal region under isoflurane anesthesia. After a recovery period of 3 to 4 days, the evolution of kidney function parameters was checked weekly until the end point date of 28 days.

All these models have in common that the induction of kidney injury is established by long term infusion of an injury inducer. Hence, the experiments easily last longer than 20 days and/or require complicated operations, rendering the drug screening inefficient and time consuming.

A modified method for the measurement of glomerular permeability in mice has been described by Königshausen et al. (Scientific Reports 6:39513, 2016, p. 1-14). In brief, anesthesized female FVB mice were catheterized and urine was collected continuously. FITC-Ficoll 70 was injected i.p., whereas AngII was applied by continuous infusion. Collected urine was subjected to fluorescence measurement and creatinine was analyzed via enzymatic assay. However, the method of Königshausen et al. remains invasive, irreversible and comparably slow. The required anesthesia has a known influence on the GFR, affecting the accuracy of the method. The drug screening for innovative fast therapeutic GFR solutions thus remains slow and similarly challenging as for anti-albuminuric drugs.

In 2009, Schock-Kusch et al. described an approach for transcutaneous determination of GFR by using fluorescein-isothiocyanate-labelled sinistrin (FITC-S) in rats. In small animal research this approach is known as tGFR (transcutaneous GFR). This model overcomes the poor water solubility of FITC-labelled inulin (FITC-I), which had been suggested as a GFR marker in a previously described animal model (Lorenz et al., Am J Physiol Renal Physiol 1999; 276: F172-F177). In brief, for marker application and blood sampling, catheters were inserted into the femoral vein and artery under intramuscular/intraperitoneal anesthesia and exteriorized at the back of the neck. Fluorescence was analyzed using a transcutaneous device capable of fluorescence detection through the small capillary system under the skin. The fluorescence decay is used for the calculation of half-life and GFR.

It is hence an object of the present invention to provide an improved, e.g., faster, reversible, less invasive, and/or more robust model for the induction of renal injury. It is another object of the present invention to provide an improved, e.g., faster, reversible, less invasive, and/or more robust method and/or system for identifying, testing or characterizing a candidate molecule for its suitability to treat renal injury. It is another object of the present invention to provide an improved, e.g., faster, reversible, less invasive, and/or more robust method and/or system for screening a population of candidate molecules for suitability to treat renal injury.

SUMMARY

According to a first aspect of the invention, there is provided a method for creating a renal injury model, wherein the method comprises the following steps: (i) inducing, in a test subject, renal injury by administering subcutaneously a bolus of a renal injury inducer, in a dosage sufficiently high to induce renal injury, (ii) determining at least the albumin creatinine ratio (ACR) in a urine sample taken from the subject, and (iii) determining from the ACR determined in step (ii) the degree of renal injury that has been induced in the test subject.

According to another aspect of the invention, there is provided a method for creating a renal injury model, wherein the method comprises the following steps: (i) inducing, in a test subject, renal injury by administering subcutaneously and/or intravenously a bolus of a renal injury inducer, in a dosage sufficiently high to induce renal injury, (ii) administering a pharmaceutically suitable fluorescent molecule to the test subject, wherein the total molecular weight of the molecule is ≥60 kDa or ≤15 kDa, preferably ≤10 kDa, (iii) determining at least the development of the transcutaneous fluorescence (TF) for the test subject, and (iv) determining from the development of the TF determined in step (iii) the degree of renal injury that has been induced in the test subject.

According to a some further aspects of the invention, there are provided methods of identifying, testing or characterizing a candidate molecule or a population of candidate molecules for their suitability to modulate or treat renal injury, wherein the methods are based on the methods to create a renal injury model as described before and wherein the methods further comprise the administration of a candidate molecule and the determination whether or not the candidate molecule is capable of modulating, alleviating or preventing the renal injury induced in the test subject based on the respective readout.

According to further aspects of the invention there are provided molecules and compositions for the modulation or treatment of renal injury and methods for producing these compositions.

BRIEF DESCRIPTION OF THE DRAWINGS

FIG. 3. Exemplary scheme of cross AGISHA experimental setup.

FIG. 4A-C. Reversibility of the AGISHA model. Results from experimental setup according to FIG. 3. Note that "n µg" refers to two boli (one i.v., one s.c.) with n µg each. FIG. 4 (A) On experimental day 1 ACR is significantly increased in urine collected for 4 hours after the first AngII bolus injections (5 µg (i.e. 5 µg i.v.+5 µg s.c.) for group 2 and 10 µg (i.e., 10 µg i.v.+10 µs.c.) for group 3) compared with the control group 1, which was injected with NaCl. FIG. 4 (B) On day 2, 24 hours after the first induction of acute glomerular injury, experimental groups 1, 2 and 3 were tested for ACR. For none of the groups the analysis shows a detectable ACR, indicating the reversibility of the injury induction after 24 h. FIG. 4 (C) On the third experimental day, the order of the stimuli was changed as shown in FIG. 3. Group 1 received the 5 µg dose (5 µg i.v.+5 s.c.) of AngII, group 2 the 10 µg dose (10 µg i.v.+10 µg s.c.) of AngII and group 3 the control injection (NaCl). As expected, the ACR data show a dose dependent increase of injury for groups 1 and 2. Group 3 shows no detectable ACR after injection with 0.9% NaCl. Mean±SD*//*/****=significant with p<0.05/0.01/0.001/0.0001 vs. NaCl (5-10 animals) (One-way ANOVA followed by Dunnett's Multiple Comparison post-hoc analysis).

FIG. 5. Scheme of AGISHA setup for positive and negative modulators as candidate molecules FIG. 6. AGISHA model with positive and negative modulators. Results from experimental setup according to FIG. 5. The graphs show a significant increase of ACR in urine collected for 4 hours after AngII bolus injection with AngII (two boli, one i.v., one s.c., with 10 µg each). ACR ratio is significantly reduced for animals pre-treated with positive modulator Enalapril. Losartan pre-treated animals show a highly significant reduction of AngII induced injury, almost comparable with the NaCl control group. Tivozanib administration shows no effect on ACR induced by AngII. N.D=no detectable ACR, mean±SD*//*/****=significant with p≤0.05/0.01/0.001/0.0001 vs. AngII (5-10 animals) (One-way ANOVA followed by Dunnett's Multiple Comparison post-hoc analysis).

FIG. 9. Scheme of AGISHA experimental setup with HPSE inhibitor as candidate molecule.

FIG. 10. AGISHA model and HPSE inhibitor. Results from experimental setup according to FIG. 9. The graph shows a significant increase of ACR in urine collected for 4 hours after AngII bolus injection in the tested animals with 10 µg AngII. Note that "10 µg" means two boli (one i.v., one s.c.) with 10 µg each. The ACR ratio was significantly reduced in animals pre-treated with the investigated HPSE inhibitor at a dose of 40 mg/kg. Losartan pre-treated animals showed a highly significant reduction of AngII induced injury, almost comparable with the control group (NaCl). N.D=no detectable ACR, mean±SD*//*/****=significant with p≤0.05/0.01/0.001/0.0001 vs. AngII (5-10 animals) (One-way ANOVA followed by Dunnett's Multiple Comparison post-hoc analysis).

FIG. 11. Scheme of AGISHA experimental setup with sGC activator candidate molecule 4-({(4-carboxybutyl)[2-(5-fluoro-2-{[4'-(trifluoromethyl)biphenyl-4-yl]methoxy}phenyl)ethyl]amino}methyl)benzoic acid.

DETAILED DESCRIPTION

Figures 1, 2:
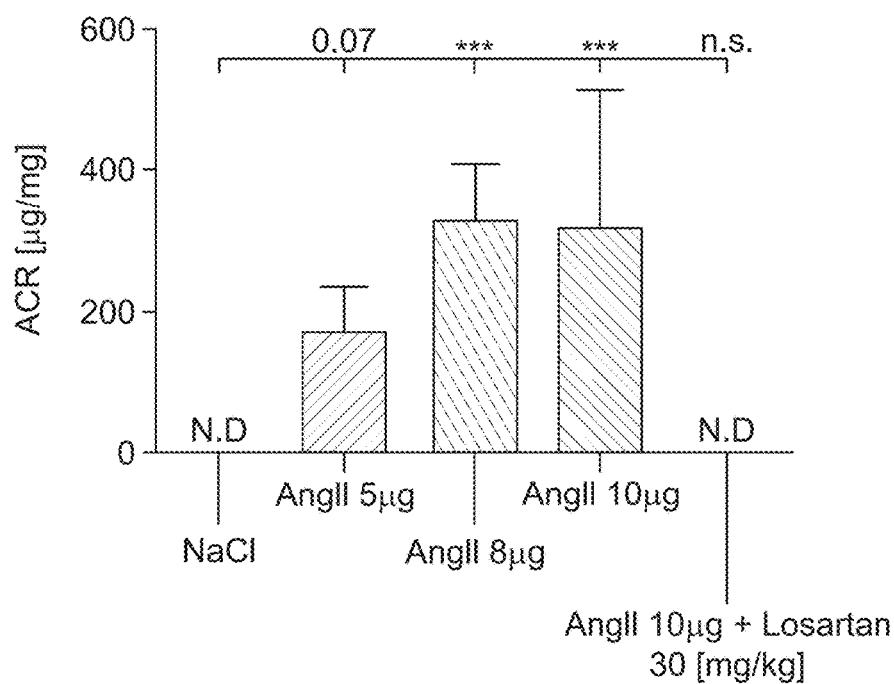
FIG. 1. Exemplary scheme of AGISHA experimental setup. AngII: Angiotensin II, i.v.: intravenous, s.c.: subcutaneous.
FIG. 2. Dose dependent effect of AngII in mouse AGISHA model. Results from experimental setup according to FIG. 1. The graph shows the significant increase of albumin/creatinine ratio (ACR) in urine collected for 4 hours after AngII bolus (i.v. and s.c.) injections in mice. Note that in this particular context "n µg" means two boli (one i.v., one s.c.) with n µg each. Doses of 8 µg (8 µg i.v.+8 µg s.c.) and 10 µg (10 µg i.v.+10 µg s.c.) result in a significant induction of ACR after the injection compared with the NaCl control group. AngII receptor antagonist Losartan prevents AngII-induced ACR induction. N.D=no detectable ACR, Mean±SD*//*/****=significant with p≤0.05/0.01/0.001/0.0001 vs. NaCl (5-10 animals) (One-way ANOVA followed by Dunnett's Multiple Comparison post-hoc analysis)

Before the invention is described in detail, it is to be understood that this invention is not limited to the particular component parts of the devices described, or process steps of the methods described, as such devices and methods may vary. It is also to be understood that the terminology used herein is for purposes of describing particular embodiments only, and is not intended to be limiting. It is moreover to be understood that, in case parameter ranges are given which are delimited by numeric values, the ranges are deemed to include these limitation values.

It is further to be understood that embodiments disclosed herein are not meant to be understood as individual embodiments which would not relate to one another. Features discussed with one embodiment are meant to be disclosed also in connection with other embodiments shown herein. If, in one case, a specific feature is not disclosed with one embodiment, but with another, this does not necessarily mean that said feature is not meant to be disclosed with said other embodiment. The skilled person would understand that it is the gist of this application to disclose said feature also for the other embodiment, but that just for purposes of clarity and to keep the specification in a manageable volume this has not been done.

It is further to be understood that where a method comprises different steps, the order of steps can be changed and all possible orders of steps are likewise meant to be disclosed. The person skilled in the art would be able to easily identify where the order of individual steps cannot be shuffled.

Furthermore, the content of the prior art documents referred to herein is incorporated by reference. This refers, particularly, for prior art documents that disclose standard or routine methods. In that case, the incorporation by reference has mainly the purpose to provide sufficient enabling disclosure, and to avoid lengthy repetitions.

Definitions

Unless otherwise defined, all scientific and technical terms used in the description, figures and claims have their ordinary meaning as commonly understood by one of ordinary skill in the art. All publications, patent applications, patents, and other references mentioned herein are incorporated by reference in their entirety. In case of conflict, the present specification, including definitions, will prevail. If two or more documents incorporated by reference include conflicting and/or inconsistent disclosure with respect to each other, then the document having the later effective date shall control. The materials, methods, and examples are illustrative only and not intended to be limiting. Unless otherwise stated, the following terms used in this document, including the description and claims, have the definitions given below.

The word "about" or "approx." as used herein refers to a value being within an acceptable error range for the particular value as determined by one of ordinary skill in the art, which will depend in part on how the value is measured or determined, i.e., on the limitations of the measurement system. For example, "about" can mean within one or more than one standard deviation, per the practice in the art. The term "about" is also used to indicate that the amount or value in question may be the value designated or some other value that is approximately the same. The phrase is intended to convey that similar values promote equivalent results or effects as described herein. In this context "about" may refer to a range above and/or below of up to 10%. Wherever the term "about" is specified for a certain assay or embodiment, that definition prevails for the particular context.

The terms "comprising", "including", "containing", "having" etc. shall be read expansively or open-ended and without limitation. Singular forms such as "a", "an" or "the" include plural references unless the context clearly indicates otherwise. Thus, for example, reference to a "candidate molecule" includes a single candidate molecule as well as a plurality of candidate molecules, either the same or different.

Unless otherwise indicated, the term "at least" preceding a series of elements is to be understood to refer to every element in the series. The terms "at least one" and "at least one of" include for example, one, two, three, four, or five or more elements. It is furthermore understood that slight variations above and below a stated range can be used to achieve substantially the same results as a value within the range. Also, unless indicated otherwise, the disclosure of ranges is intended as a continuous range including every value between the minimum and maximum values.

The "Glomerular Filtration Barrier" (GFB) is the physiological filter of the basic kidney subunit called nephron. The GFB is responsible for the filtration of substances including toxins from the peripheral blood into the pre-urine while retaining the proteins and cellular components of the blood. The GFB is a three part fenestrate fibro-cellular membrane composed of three different components. (i) The glomerular capillary endothelial cell barrier serves as first blood capillary filtering tool. (ii) The glomerular basement membrane (GBM), a multi-collagenous membranous serves as support of the adjacent filtration components and (iii) the glomerular visceral epithelia cell barrier (known as podocyte-podocyte filtration barrier) serves as sieving tool inside the glomerulus and is responsible for the last filtration step. The glomerular filtrate is then collected in a cavity within the glomerular capsule called Bowman's space. The GFB is responsible for maintaining the protein concentration in the blood stream by avoiding their passage into the pre-urine inside the Bowman's space. With a molecular weight beyond the filtration size limit of approx. 60 kDa to 70 kDa molecules cannot pass.

The "glomerular filtration rate" (GFR) is the volume of fluid filtered from the glomerular capillaries into the Bowman's capsule per unit time. The GFR is therefore an important marker of kidney function. In clinical use, the GFR levels are used for staging of chronic kidney disease. GFR can be measured indirectly as the clearance of filtration markers that are eliminated by the kidney only by glomerular filtration. Preferably, such a marker is freely filtered at the glomeruli and neither secreted nor reabsorbed by the renal tubules. Measuring GFR typically occurs based on biochemical analysis of repeatedly collected blood and urine samples and estimation of the component Creatinine. GFR can also be measured using radioactive substances, in particular Chromium-51 and Technetium-99m. These come close to the ideal properties of inulin (undergoing only glomerular filtration) but can be measured more practically with only a few urine or blood samples.

"Creatinine" is a constantly produced byproduct of muscle metabolism and is removed from the blood mainly by the kidneys, primarily by glomerular filtration, but also by proximal tubular secretion. Little or no tubular reabsorption of creatinine occurs. If the filtration in the kidney is deficient, creatinine blood levels rise. Therefore, creatinine levels in blood and urine may be used to calculate the creatinine clearance (CrCl), which correlates approx. with the GFR (10%-20% deviation).

"Inulin" is an exogenous filtration marker derived from a fructose polymer and is a physiologically inert substance. Although inulin clearance is considered the gold-standard method for assessing GFR in patients, the need for continuous infusion, multiple blood samples and urine collection, make it cumbersome and expensive to measure. This has led to some research to develop alternative methods based on different biomarkers.

Like inulin the polymer "sinistrin" is not metabolized in human blood and passes the kidneys unchanged. The average molecular is at 3500 Da with a range from 2000 to 6000 Da. Sinistrin is an inulin-type β-D-fructan with branches on position 6. Main differences between sinistrin and inulin are the higher alkali-resistance, a better water solubility and easier handling of sinistrin compared to inulin.

"Albumin" is a globular serum protein with an approximate molecular weight of 65 kDa. Albuminuria occurs when the kidney leaks small amounts of albumin into the urine, i.e., when there is an abnormally high permeability for albumin in the glomerulus of the kidney. To compensate for variations in urine concentration, the albumin concentration in the urine sample can be normalized to the concentration of creatinine, which is constant even under the conditions described above. The resulting "albumin/creatinine ratio" (ACR) can be used as readout parameter for albuminuria. The determination of protein content from the urine samples can be assessed by any method known in the art. Methods known in the art to determine albumin and creatine content comprise immunologic methods such as ELISA or radioimmunoassay, mass spectrometry based methods and a variety of other methods. Various devices or urine test strips are likewise available to directly assess the ACR.

The term "renal injury" comprises structural and functional alterations affecting the physiological function of the kidney. In particular, these structural changes may involve one or more structural component(s) of the GFB. Renal injury can be measured by a variety of methods known in the art. Occurrence of albuminuria, a detectable amount of ACR or a change in GFR are some of the symptoms of renal injury.

A "renal injury model" is an animal model to study renal injury. For instance, such a model can be used for the development of novel drugs or modulators of different types of renal disease. It can furthermore be used to determine potential renal toxicity of compounds. Suitable subjects for such a renal injury model are all non-human animals with a renal system which is structurally and/or functionally comparable with the human renal system. Suitable subjects are all non-human animals that can be used to mimic the mechanisms of human renal disease. Preferably, the subject of a renal injury model is a pig, a monkey, a dog, a sheep, a rabbit or a rodent, such as a rat or a mouse. For instance, the subject of a renal injury model can be a rat, such as a Wistar Kyoto rat or a mouse, such as a C57Bl/6 mouse.

The term "renal injury inducer" or "inducer of renal injury" as used herein refers to any composition, compound or molecule suitable to induce renal injury. For example, the injury inducer can be a small molecule or a biomolecule, such as an antibody. The ability of kidneys to concentrate and metabolize chemicals makes them particularly prone to toxic damage. Molecules can have renal toxicity in a variety of ways, including having deleterious effects on the vasculature, GBM, glomerular cells, and tubular epithelium. A variety of toxic compounds and substances is known in the art and can be used to establish a renal injury model system, including GBM toxins, podocyte toxins (e.g. adriamycin), tubular toxins (e.g. cisplatin, mercuric chloride, gentamicin) or substances leading to tubular obstruction (e.g. by long term feeding of adenine, or IP injection of folic acid). For example, the renal injury inducer may be an inducer of GFB injury, such as angiotensin. Of note, the applied dose of a substance may have an impact on the type of injury, i.e. depending on the dose different renal structures may be affected. For example, at the concentration applied the renal injury inducer vasopressin may be an inducer of GFB injury in a subject. In yet another example, at the concentration applied the renal injury inducer Sema3a may be an inducer of podocyte injury in a subject. In a further example, at the concentration applied the renal injury inducer heparanase may be an inducer of endothelial cell injury in a subject.

The term angiotensin II (AngII) comprises the peptide hormone of the sequence Asp-Arg-Val-Tyr-Ile-His-Pro-Phe. In particular, the term AngII refers to human angiotensin II or a derivative thereof. Angiotensin II can directly constrict vascular smooth muscle cells, stimulate aldosterone production, activate the sympathetic nervous system and increase sodium reabsorption, all of which are mediated through AngII type (AT) 1 receptor activation, and can contribute to the development of hypertension. In addition to its hypertensinogenic effect, locally produced AngII in the kidney can activate multiple intracellular signaling pathways and induce inflammation, renal cell growth, mitogenesis, apoptosis, migration and differentiation. These effects of AngII can also be mediated through AT1 receptor activation and play an important role in the pathogenesis of renal tissue injury. In the long-term model described by Rippe C et al 2007, AngII is used to develop a damage of the glomerular basement membrane (GBM).

"Antidiuretic hormone", also known as "Vasopressin" (AVP), is a nine amino acid peptide secreted from the posterior pituitary. As used herein, the term also comprises vasopressin and derivatives thereof as well as AVP salts, such as ARG8-vasopressin acetate salt. Vasopressin is essential for cardiovascular homeostasis, acting via the kidney to regulate water resorption and on the vasculature to regulate smooth muscle tone. AVP can bind to receptors of its target cells in the kidney tubules and vascular smooth muscle. Vasopressin can bind with three different receptors ($V_1A$, $V_1B$, and $V_2$). Vasopressin-$V_1$ binding is caused by decreased vessel tone, decreased vascular resistance and decreased blood pressure. $V_1$ receptors are found in blood vessels and binding stimulates vasoconstriction. Vasopressin-$V_2$ binding is caused by an increase in plasma osmolarity. Vasopressin binding to $V_2$ receptors stimulates the G-protein coupled cAMP second messenger system. This system increases the concentration of cAMP in the collecting ducts of the kidney, creating aquaporins (AQP-Z) by exocytosis, allowing for water reabsorption and vasculature constriction. The activation of these receptors during kidney disease plays an important role in the pathogenesis of renal tissue injury.

The term "Sema3a" refers to the protein Semaphorin-3A. The Sema3a protein is encoded by the gene SEMA3A. Alternative names for the Sema3a protein comprise Sema3A, Semaphorin III and Sema II. Alternative names for the gene SEMA3A comprise SEMAD. The Sema3a protein comprises human, rat, murine and further mammalian and non-mammalian homologues. Sequence(s) for human Sema3a are accessible via UniProt Identifier Q14563 (SEM3A_HUMAN), for instance human isoform Q14563-1. Sequence(s) for murine Sema3a are accessible via UniProt Identifier O08665 (SEM3A_MOUSE), for instance murine isoform O08665-1. Different isoforms and variants may exist for the different species and are all comprised by the term Sema3a. In addition, synthetic or maturated variants of the Sema3a protein may be generated and are comprised by the term Sema3a. The protein Sema3a may furthermore be subject to various modifications, e.g, synthetic or naturally occurring modifications. Examples for modifications are known in the art and include for example phosphorylation, glycosylation and lipidation. Recombinant Sema3a is commercially available or can be manufactured as known in the art.

The term "heparanase" refers to the protein heparanase. The heparanase protein is encoded by the gene HPSE. Alternative names for the heparanase protein comprise Endo-glucoronidase and Heparanase-1. Alternative names for the gene HPSE comprise HEP, HPA, HPA1, HPR1, HPSE1, HSE1. The heparanase protein comprises human, rat, murine and further mammalian and non-mammalian homologues. Sequence(s) for human heparanase are accessible via UniProt Identifier Q9Y251 (HPSE_HUMAN), for instance human isoform Q9Y251-1. Sequence(s) for murine heparanase are accessible via UniProt Identifier Q6YGZ1 (HPSE_MOUSE), for instance murine isoform Q6YGZ1-1. Different isoforms and variants may exist for the different species and are all comprised by the term heparanase. In addition, synthetic or maturated variants of the heparanase protein may be generated and are comprised by the term heparanase. The protein heparanase may furthermore be subject to various modifications, e.g, synthetic or naturally occurring modifications. Examples for modifications are known in the art and include for example phosphorylation, glycosylation and lipidation. Recombinant heparanase is commercially available or can be manufactured as known in the art.

An "intravenous" (i.v.) injection as used herein refers to a method to deliver liquid substances as a bolus directly into a vein. In rodents, the i.v. injection can be performed using the tail vein of the subject. For convenience commercially available restraint devices can be used for application. The tail can be warmed, e.g. with a heating source, to help dilate the veins. Based on the subject there is a restriction regarding applicable injection volumes. For instance, the maximal volume for i.v. injections can be 0.2 ml in mice and 0.5 ml in rats.

A "subcutaneous" (s.c.) injection as used herein refers to an injection which is administered as a bolus into the subcutis, the layer of skin directly below the dermis and epidermis, collectively referred to as cutis. For mice, the most usual site for injection is over the shoulders, into the loose skin over the neck, but other sites with loose folds of skin can also be used, for example over the flank. Maximal volumes for subcutaneous injection in the back scruff may be 2 to 3 ml in mice and 5 to 10 ml in rats. When repeated doses of material are needed, varying the site of injection can help to reduce the likelihood of local skin reactions.

The term "Transcutaneous fluorescence" (TF) as used herein refers to the fluorescence that passes through the (intact) skin. The measurement of TF can be performed using a transcutaneous LED detecting fluorescence device or any other method suitable in the art. For example, a transcutaneous device capable of fluorescent detection through the small capillary system under the skin can be used as described by Schock-Kusch et al. To overcome auto-fluorescence of hairs, the hair can be removed, e.g. by depilation or shaving. A detailed description of the measurement of the TF is incorporated herein by reference as found in Rajagopalan R et al., Chronic Kidney Disease, edited by M. Gooz (Intech, Rijeka, Croatia 2012), Chapter 15, p. 251-260, Daniel Schock-Kusch et al., Nephrol Dial Transplant., 24(10), 2009, p. 2997-3001. The development of TF can be assessed by repeated or continuous measurement of TF over a certain period of time.

A "fluorescent molecule" as used herein is any compound which emits light after it has absorbed light or other electromagnetic radiation. The fluorescent molecule can either be intrinsically fluorescent, such as a fluorescent protein, or can be composed of different parts, wherein at least one portion is fluorescent. For example, the fluorescent molecule may comprise a fluorescent label, such as fluorescein isothiocyanate (FITC) or another fluorescein derivative. The fluorescent molecule may further comprise a polymer, such as inulin, sinestrin or Ficoll.

The term "Ficoll" as used herein is a neutral, highly branched, high-mass, hydrophilic polysaccharide which dissolves readily in aqueous solutions. It is prepared by reaction of the polysaccharide with epichlorohydrin. For Ficoll the number behind the name typically indicates the average molecular weight (e.g. 400000+/−100000 for Ficoll 400).

As used herein, the expression "pharmaceutically suitable/acceptable" refers to those active compounds, materials, compositions, carriers, and/or dosage forms which are, within the scope of sound medical and ethical judgment, suitable for use in contact with the tissues of the non-human test subject and/or a human patient without excessive toxicity, irritation, allergic response, or other problems or complications.

The term "pharmaceutical composition" as used herein relates to a pharmaceutically acceptable composition for administration to a subject, preferably a human patient. In some preferred embodiments the pharmaceutical composition comprises a composition for parenteral, transdermal, intraluminal, intraarterial or intrathecal administration or for direct injection into tissue. In particular it is envisaged that said pharmaceutical composition is administered to a patient via infusion or injection. Administration of the suitable compositions may occur by different ways, such as by intravenous, intraperitoneal, subcutaneous, intramuscular, topical or intradermal administration. The pharmaceutical composition according to the current invention may further comprise a pharmaceutically acceptable carrier. Compositions comprising a suitable pharmaceutically acceptable carrier can be formulated using conventional methods well known in the art. Examples of a suitable pharmaceutically acceptable carrier are likewise well known in the art and include phosphate buffered saline solutions, isotonic solutions, aqueous solutions, emulsions, wetting agents, sterile solutions etc. These pharmaceutical compositions can be administered to the subject at a suitable dose. The dosage regimen can be determined by the attending physician in view of the relevant clinical factors. Factors that may influence such a dosage regimen include size, weight, body surface area, age and sex of the subject or patient as well as time and route of administration.

Embodiments

According to the current invention, there are provided short-term renal injury models and methods for creating these models. Combinations of minimal invasive injury induction and non-invasive readout methods resulted in surprisingly fast and reversible model systems. Compared to some or all of the methods known from the literature, the methods and models provided herein are thus reversible, faster and/or less invasive. They require less handling, minimal or no anesthesia and/or are not inherently terminal for the subject of the renal injury model. Furthermore, the models according to the current invention are suitable to simulate different diseases and degrees of disease, e.g. based on type and dosage regimen of the injury inducer.

According to a first aspect of the invention, there is provided a method for creating a renal injury model, wherein the method comprises the following steps:
a) inducing, in a test subject, renal injury by administering subcutaneously a bolus of a renal injury inducer, in a dosage sufficiently high to induce renal injury,
b) determining at least the albumin creatinine ratio (ACR) in a urine sample taken from the subject, and
c) determining from the ACR determined in step b) the degree of renal injury that has been induced in the test subject.

Figure 8:
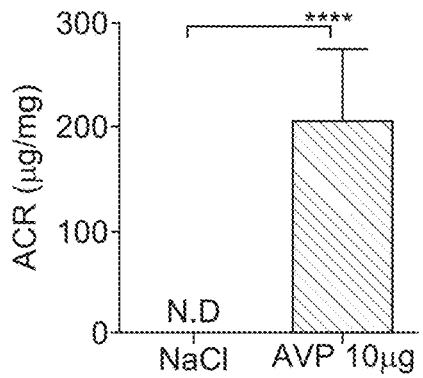
FIG. 8. AGISHA model injury induced by AVP. Results from experimental setup according to FIG. 7. The graph shows a significant increase of ACR in urine collected for 4 hours after AVP bolus injection with 10 µg per injection (10 µg i.v.+10 µg s.c.). N.D=no detectable ACR, mean±SD*//*/****=significant with p≤0.05/0.01/0.001/0.0001 vs. NaCl (5-10 animals) (unpaired T-test).

The inventors have called said model "Acute glomerular inducible short term albuminuria model", abbreviated as "AGISHA" herein. Being less time-consuming and technically easy to handle, administration of a renal injury inducer based on single injections e.g. subcutaneous or intravenous injection or a combination of s.c. and i.v. injections is advantageous over the state of the art, where continuous infusion, e.g. using minipumps, is commonly used. For the subcutaneous administration of the renal injury inducer both, handling and technical procedure are robust and efficient. Being only minimally invasive, subcutaneous administration often causes only minimal pain or discomfort for the animal. For the current invention, handling and administration route(s) preferably require no or only minimal amounts of anesthesia. For instance, mechanical restraint or an anesthesia protocol using 3% isoflurane/air mixture can be used, e.g. for AngII injection. For example, FIGS. 2 and 8 show the successful induction of renal injury in a subject. Surprisingly, intravenous and/or subcutaneous administration of the renal injury inducer by single injection(s) leads to significant induction of renal injury. This finding was particularly surprising, because the rate of absorption of an injury inducer depends on the route of administration.

In some embodiments according to the different aspects of the current invention, the subject of the renal injury model is a pig, a monkey, a dog, a sheep, a rabbit or a rodent, such as a rat or a mouse. In some embodiments according to the different aspects of the current invention, the subject of the renal injury model is a rat, such as a Wistar Kyoto rat or a mouse, such as a C57Bl/6 mouse, or another rodent. For each of the different aspects according to the current invention, there are some preferred embodiments wherein the test subject(s) are rodents, preferably mice or rats.

The renal injury inducer described for the different aspects of the current invention can be any composition, compound or molecule suitable to induce renal injury. Examples for different injury inducer classes and compositions are described herein. In some embodiments, the injury inducer is a protein or a small molecule. In some embodiments, the injury inducer is a podocyte toxin, a tubular toxin or any other composition, compound or molecule leading to structural changes of the GFB and/or the GBM. In some embodiments, at the concentration applied, the renal injury inducer is an inducer of GBM injury. In some embodiments, at the concentration applied, the renal injury inducer is an inducer of podocyte injury. In some embodiments, at the concentration applied the renal injury inducer is an inducer of endothelial cell injury. According to some embodiments of the invention, the renal injury inducer is selected from the group consisting of Angiotensin II, and/or Vasopressin, and/or Sema3a, and/or heparanase. Determination of a suitable concentration of the injury inducer mainly depends on the type of injury inducer and on the subject and can be determined by dose optimization as shown in FIGS. 1 and 2.

In some preferred embodiments the described injury inducer is AngII, such as human angiotensin II, or a derivative thereof. In some embodiments, the total dose of the AngII is in the range of between ≥5 and ≤55 µg/mouse (which is about between ≥0.17 and ≤3.66 µg/g), or in the range of between ≥3 and ≤35 µg/rat. In some embodiments, AngII is administered s.c. at a single dose of 40 µg/mouse to induce renal injury.

In some preferred embodiments, vasopressin or a salt thereof, such as (ARG8)-vasopressin acetate salt (AVP) is used as a renal injury inducer. So far, AVP has not been described as a renal injury inducer for use in a respective model. FIG. 8 shows the successful induction of renal injury with injury inducer AVP. In some embodiments of the invention, the total dose of vasopressin or the salt thereof is in the range of between ≥5 and ≤35 µg/mouse (which is about between ≥0.17 and ≤1.16 µg/g).

Figure 18:
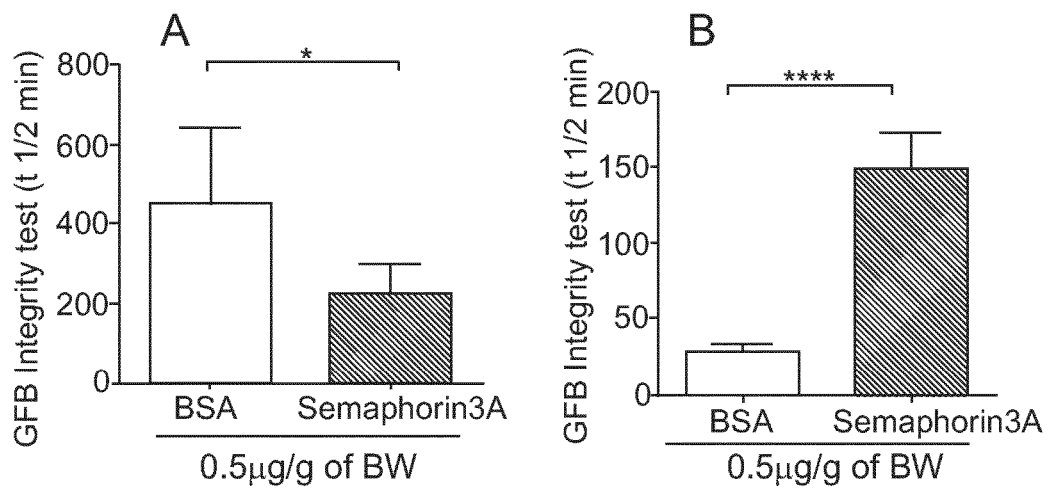
FIG. 18. Injury inducer Sema3a reduces GBM integrity and induces ACR in the respective models. The graphs show (A) a significantly decreased half-life for fluorescent molecule Ficoll-FITC 2 hrs after Sema3a bolus injection (0.5 µg/g bodyweight) and (B) a significantly increased ACR in the tested animals in comparison with bovine serum albumin (BSA) control. Mean±SD*//*/****=significant with p≤0.05/0.01/0.001/0.0001 vs. BSA Vs Sema3a (5-10 animals) (unpaired T-test).

AngII induced GBM damage is a fast and stable trigger method to mimic human hypertensive glomerular disease or complications. However, a non-hypertensive trigger is required to study non-hypertensive kidney pathologies. The ability of Sema3a to induce non hypertensive injury of the GBM and albuminuria has been described by Tapia R et al., Kidney International, 73(6), 2008, p. 733-740. Recombinant Sema3a as a trigger to mimic human hypertensive glomerular disease has a known mode of action, leads to a fast onset of injury, can be injected in rodents, and damages the integrity of the GBM (FIG. 18). Example 8 as well as FIGS. 18, 19 and 20 describe the experimental scheme and successful induction of renal injury with injury inducer Sema3a according to the models and methods of the current invention. In some embodiments, the injury inducer is Sema3a, such as recombinant Sema3a. In some embodiments, the injury inducer is Sema3a and the total dose of Sema3a is approx. 0.5 µg/g of bodyweight (BW) of the subject. In some embodiments, renal injury is induced by a single injection, such as an i.v. injection, of recombinant Sema3a.

The extracellular matrix (ECM) plays a key role in both normal and disease processes as diverse as angiogenesis, inflammation, wound healing and tumor cell invasion. In the ECM, heparan sulphate proteolglycans (HSPGs) interact with fibronectin, laminin, collagen and growth factors to help maintain cellular architecture. One of the key enzymes involved in specifically degrading the heparan sulphate (HS) component of the ECM is the endo-b-glucuronidase enzyme heparanase. The glomerular endothelium is highly fenestrated and the fenestrae are filled with dense glycocalyx. The glycocalyx maintains the protein filtration barrier at this site. Heparan sulfate is the key polysaccharide within the glycocalyx and keeps the filtration barrier intact. Overexpression of HPSE leads to albuminuria in unchallenged genetically overexpressing HPSE transgenic mice (HPSEtg) and increased kidney damage after I/R injury in HPSEtg (van den Hoven et al, Kidney Int, 70(12), 2006, p. 2100-8, van den Hoven et al, Kidney Int, 73, 2008, p. 278-287, Masola et al., PlosOne, 11(7), 2016, e0160074). Increased HPSE markedly reduced HS expression in the kidney and leads to significant higher levels of albuminuria during glomerular injury. In some embodiments, the injury inducer is heparanase, e.g. recombinant active heparanase. In some embodiments, HPSE is applied at a dose of 0.8 mg/kg to induce the renal injury.

For each aspect of the current invention there are provided some embodiments, wherein the method besides a subcutaneous injection further comprises the intravenous administration of a second bolus of the same or a different renal injury inducer, in a dosage sufficiently high to induce renal injury together with the subcutaneous bolus of the first renal injury inducer. For each of the aspects of the current invention, there are some embodiments, wherein the two boli are administered simultaneously, or in sequence. In some of these embodiments, the two boli comprise the same renal injury inducer. However, it can likewise be provided that the two boli comprise different renal injury inducers. In some embodiments, the two boli comprise an identical dosage. However, it can likewise be provided that the two boli comprise different dosages. In some preferred embodiments, the dosage comprised in the intravenous bolus is smaller than the dosage comprised in the subcutaneous bolus. In these embodiments, the intravenous bolus may act as a first inducer, while the subcutaneous bolus then evokes the actual symptoms of renal injury.

For some embodiments, the first and/or a second renal injury inducer is selected from the group consisting of Angiotensin II, Vasopressin, Sema3a and heparanase, preferably human Angiotensin II, (ARG8)-vasopressin salt (AVP), recombinant Sema3a and recombinant heparanase.

In some preferred embodiments, the total dose of the one or two boli of AngII is in the range of between ≥5 and ≤55 µg/mouse (which is about between ≥0.17 and ≤3.66 µg/g), and/or in the range of between ≥3 and ≤35 µg/rat. This means that, in case two boli are used, the individual doses can be for example in the range of ≥2.5 and ≤45 µg/mouse, or in the range of ≥1.5 and ≤28 µg/rat.

In some preferred embodiments, (ARG8)-vasopressin salt (AVP) is used as a renal injury inducer. In some preferred embodiments, the total dose of one or two boli of vasopressin is in the range of between ≥5 and ≤35 µg/mouse (which is about between ≥0.17 and ≤1.16 µg/g). This means that, in case two boli are used, the individual doses can be in the range of ≥2.5 and ≤25 µg/mouse.

An important characteristic of a renal injury model is the readout for the degree of renal injury. For the AGISHA model, the Albumin/creatinine ratio was used as readout. However, as discussed below, the AGISHA model can be adapted, for example such that GFR is used as readout. Albumin is a protein that is present in high concentrations in the blood. Virtually no albumin is present in the urine when the kidneys are functioning properly. However, albumin may be detected in the urine even in the early stages of kidney disease (albuminuria). Creatinine, a byproduct of muscle metabolism, is normally released into the urine at a constant rate and its level in the urine is an indicator of the urine concentration. Creatinine levels can therefore be used to correct for urine concentration in a random urine sample. For human patients, the American Diabetes Association has stated a preference for the albumin/creatinine ratio (ACR) for screening for albuminuria indicating early kidney disease.

The determination of the albumin creatinine ratio (ACR) is preferably carried out using routine analysis after urine collection. For example, following the induction of renal injury, e.g., with AngII, test subjects are placed within metabolic cages for up to 4 hours. In some preferred embodiments, urine of the subject is collected non-invasively for ≥0.25, ≥1, ≥2, ≥3, ≥4, ≥5 or ≥6 hours. According to some embodiments of the invention, the collection of urine for the determination of the ACR is carried out between ≥2 hrs and ≤6 hrs after administration of the first bolus of injury inducer. According to some embodiments of the invention, the collection of urine for the determination of the ACR is carried out between ≥0 hrs and ≤12 hrs after administration of the first bolus.

The collected urine is analysed by an automatic analyser for urinary albumin (automatic enzyme-linked immunosorbent assay method or any other suitable method known in the art) as well as urinary creatinine (any suitable method known in the art, such as an enzyme method, such as Cobas® Integra 400 (Roche, Basel, Switzerland) or via ELISA (e.g. Mouse albumin ELISA kit, ABCAM, Cambridge, UK). ACR is calculated by dividing the obtained albumin concentration by the obtained creatinine concentration.

Based on the ACR the degree of renal injury can be determined. For the AGISHA model, the ACR can be used as a direct measure for the degree of renal injury. In one embodiment the ACR determined in one or more test subjects is compared to the ACR of one or more control subjects wherein renal injury has not been induced, e.g., because the bolus administered comprised only saline. In one embodiment the ACR determined in one or more test subjects is compared to reference values for ACR, wherein these reference values have been acquired for healthy control subjects in a comparable setup of the AGISHA model.

For the animal model according to the first aspect, the primary readout parameter ACR is obtained after 4 hours, leading to a fundamentally reduced expenditure of time for the model. Compared with the ureter cannulation proposed by prior art models, the use of metabolic cages is less invasive and does not require anesthesia. Thus, the model allows reversible short term induction of renal injury for the study of renal injury, and is hence advantageous over the methods in the prior art.

According to a second aspect of the invention, there is provided a method for creating a renal injury model, wherein the method comprises the following steps:
 a) inducing, in a test subject, renal injury by administering subcutaneously and/or intravenously a bolus of a renal injury inducer, in a dosage sufficiently high to induce renal injury,
 b) administering a pharmaceutically suitable fluorescent molecule to the test subject, wherein the total molecular weight of the molecule is ≥60 kDa,
 c) determining at least the development of the transcutaneous fluorescence (TF) for the test subject, and
 d) determining from the development of the TF determined in step c) the degree of renal injury that has been induced in the test subject.

Figure 15:
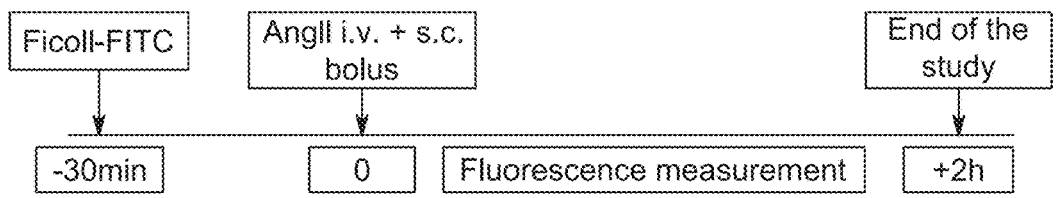
FIG. 15. Scheme of GFBI test model setup.

The model system according to the second aspect was called GFBI test model and can be used to evaluate the Glomerular Filtration Barrier Integrity. The model is a short time model with a time frame of 2 hours in total. A general scheme of the GFBI test model setup is described in Example 7 and FIG. 15. For the second aspect according to the current invention, the readout system is based on the measurement of transcutaneous fluorescence (TF) after administration of a fluorescent molecule to the subject, where the clearance of the fluorescent molecule depends on the degree of renal injury of the subject. This readout system can be used independently or in combination with the readout system according to the first aspect of the current invention.

Figure 17:
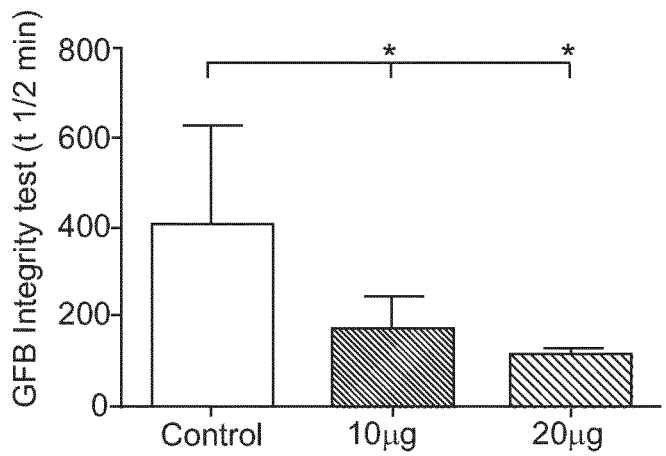
FIG. 17. Dose dependent effect of AngII on GFB integrity in a mouse GFBI test model. The graph shows the significant decrease in half-life of the applied fluorescent molecule in the blood 2 h after AngII bolus injection in the tested animals. The decrease in half-life of the fluorescent molecule was significant after injury induction with AngII (10 µg or 20 µg). Mean±SD*//*/****=significant with p≤0.05/0.01/0.001/0.0001 vs. control (5-10 animals) (One-way ANOVA followed by Dunnett's Multiple Comparison post-hoc analysis). Groups as described in example 7.
Figure 20:
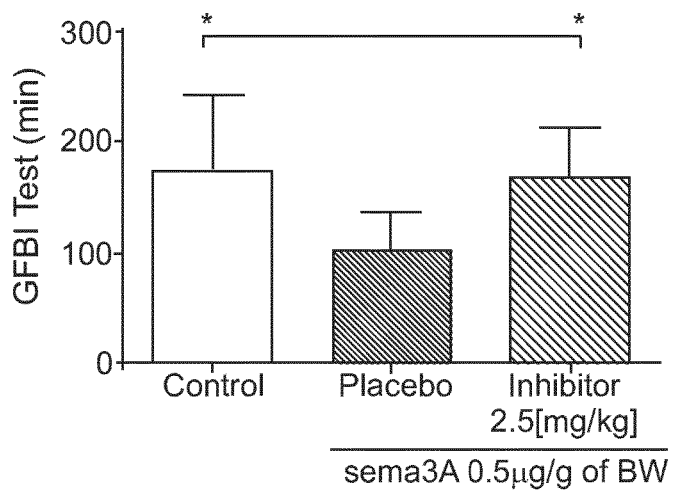
FIG. 20. Pharmacological inhibition of GBM disruption by recombinant mouse Sema3a. Results from experimental setup according to FIG. 19. The graphs show a significant decrease in half-life for the fluorescent molecule 2 hrs after Sema3A bolus injection (0.5 µg/g body weight). Administration of Sema3a inhibitor peptide (2.5 mg/kg) as candidate molecule rescued the effect of Sema3a. Mean±SD*//*/ ****=significant with p≤0.05/0.01/0.001/0.0001 vs. Placebo (5-10 animals) (One-way ANOVA followed by Dunnett's Multiple Comparison post-hoc analysis).

The descriptions, embodiments, advantages and examples relating to step a) of the method according to the first aspect likewise apply for the step a) of the method according to the second aspect. In particular all descriptions, embodiments, advantages and examples regarding the subject of the model, the administration, type and dose of the injury inducer, likewise apply for the invention according to the second aspect. For the GFBI model FIGS. 17, 18 and 20 show successful injury induction after administration of AngII, AVP, or Sema3a. As shown in example 8, the GFB integrity test as well as the AGISHA model according to the first aspect, performed as hypertensive or non-hypertensive model, show a fast and dose dependent response to the injury trigger. Moreover, it was possible to demonstrate the reversibility of the injury with appropriate tool compounds. Furthermore, the injury induction was completely reversible with the possibility to perform several consecutive experiments with the tested animals.

The fluorescent molecule described for the second aspect of the current invention is a pharmaceutically suitable fluorescent molecule or a composition thereof. Preferably, the fluorescent molecule can't cross a fully functional glomerular filtration barrier for the subject species at hand, but can cross a glomerular filtration barrier after renal injury. In some embodiments, the fluorescent molecule can't cross a fully functional glomerular filtration barrier for the subject species at hand, but can cross after endothelial injury, after podocyte injury, and/or after GFM injury. In some preferred embodiments, the pharmaceutically suitable, fluorescent molecule has a molecular weight of ≥60 kDa or ≥70 kDa. In some preferred embodiments, the pharmaceutically suitable, fluorescent molecule has a(n) (average) molecular weight of approx. ≥55, ≥56, ≥57, ≥58, ≥59, ≥60, ≥61, ≥62, ≥63, ≥64, ≥65, ≥66, ≥67, ≥68, ≥69, ≥70, ≥71, ≥72, ≥73, ≥74, ≥75, ≥76, ≥77, ≥78, ≥79 or ≥80 kDa, wherein in this particular context, the term approx. refers to +/−1 kDa. In some embodiments, said molecule comprises a polymer. In some embodiments said molecule comprises Ficoll. In some of these embodiments said Ficoll has a(n) (average) molecular weight of approx. ≥60 kDa or ≥70 kDa. In some embodiments said molecule comprises a Fluorescein isothiocyanate (FITC) or any other fluorescent dye suitable for detection. In a preferred embodiment the pharmaceutically suitable, fluorescent molecule comprises a polymer such as Ficoll and a fluorescent dye such as FITC.

According to the current invention, administering a fluorescent molecule to a test subject can occur by any suitable method known in the art. Suitable methods include but are not limited to intravenous, intraperitoneal and oral application. In some preferred embodiments, administering a fluorescent molecule to a test subject occurs by injection, such as i.v. injection. In some preferred embodiments, administration of the pharmaceutically suitable, fluorescence-labeled molecule does not require anesthesia but can occur using mechanic restraint of the subject.

Preferably, according to the current invention where administration of at least one compound is required, small volumes are injected, e.g. via tail vein injection where the subject is a rodent. Preferably, according to the current invention where administration of at least one compound is required, the number of repetitions for injections shall be minimized A method is less stressful for the test subject, if only small amounts of injection volume are applied and/or the number of repetitions for injections is kept low. In some embodiments, the pharmaceutically suitable, fluorescent molecule is applied prior to, simultaneously with or after applying at least a part of the renal injury inducer. In some embodiments, at least a part of the renal injury inducer is administered simultaneously with at least a part of the pharmaceutically suitable fluorescent molecule (see FIG. 19). In some embodiments, the pharmaceutically suitable, fluorescent molecule is applied intravenously and simultaneously with at least a part of the renal injury inducer. In some embodiments, at least a part of the pharmaceutically suitable, fluorescent molecule is combined with at least a part of the renal injury inducer prior to administration. In some embodiments, combining the pharmaceutically suitable, fluorescent molecule with the renal injury inducer occurs by mixing the components in solution, for example in the ratio 1 to 1. For instance, the fluorescent molecule is concentrated by a factor of 2 and mixed in a 1 to 1 ratio with an injury inducer such as angiotensin II, in a pharmaceutically suitable solution, such as 0.9% NaCl solution in water for injection. In some embodiments according to the second aspect, two single acute bolus injections are used for injury induction, such as, if human AngII is used, one intravenous bolus, which can furthermore be combined with the Ficoll-FITC or another fluorescent molecule, and a second subcutaneous bolus.

In some embodiments, measurement of the TF occurs with a transcutaneous LED detecting fluorescence device or any other method suitable in the art. For example, measurement of the TF can be performed as described in example 7. For some embodiments, for the measurement of the TF the device is placed on the left dorsal back side of the animal. For some embodiments, the animal is partially or fully depilated or shaved to access the derma under the hairs. For some preferred embodiments according to the second aspect, the model subject is awake during TF measurement.

Measurement of TF can be started immediately after trigger, i.e. after the fluorescent molecule has been administered. In some embodiments measurement of TF is started before, simultaneously with, or after administration of at least a part of the injury inducer.

Figure 16:
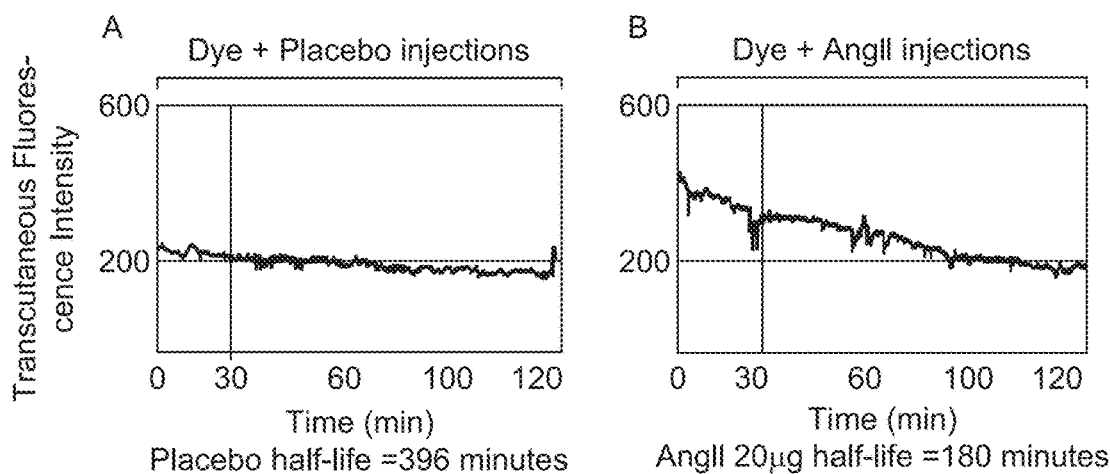
FIG. 16. Transcutaneous fluorescence (TF) in the GFBI test model after AngII injury induction. Results from experimental setup according to FIG. 15. Representative curves of TF from Ficoll-FITC dye (A) without and (B) after AngII injury induction.

To determine the development of the TF (e.g. decay or half-life of the fluorescent molecule), the measurement of TF has to be performed either continuously or with single measurements over a certain time. In some embodiments, the continuous or discontinuous measurement(s) of TF occurs for less than approx. 1, 2, 3, 4, 5, 6, 7, 8 or 24 hours, wherein for this particular context, the term "approx." refers to +/−30 min. In some preferred embodiments, the measurement of the TF occurs for ≤2 hours (FIG. 16). In some embodiments, the measurement of the TF occurs for approximately 30 minutes.

The half-life of the fluorescent molecule can be determined based on the fluorescence intensity as known in the art and as shown for instance in FIG. 16. The faster the decay in TF and the lower the half-life of the fluorescent molecule in the blood is, the higher is the degree of renal injury. Based on the development of the TF in a group of treated animals compared to a control group, the degree of renal injury can be assessed (see for example FIG. 17). In some embodiments, for an experimental group, the development of the TF and/or the half-life of the fluorescent dye Ficoll-FITC in the peripheral blood compartment is compared with an experimental control group.

Furthermore, there is provided a third aspect according to the current invention, wherein the main steps of the second aspect are maintained, while the readout system is slightly modified. More specifically, the third aspect of the current invention is based on the development of the TF as an indicator for glomerular filtration rate as readout parameter(s). It has been shown that loss or partial damage of the functional units of the kidney (nephrons) leads to a significant reduction of GFR. Loss or damage of the nephrons is difficult to monitor and the GFR remains the gold standard to indirectly measure this pathological effect. Modulation of the GFR can be modeled in rodents, but these are typically long and complex CKD models.

According to a third aspect of the invention, there is provided a method for creating a renal injury model, wherein the method comprises the following steps:
a) inducing, in a test subject, renal injury by administering subcutaneously and/or intravenously a bolus of a renal injury inducer, in a dosage sufficiently high to induce renal injury,
b) administering a pharmaceutically suitable fluorescent molecule to the test subject, wherein the total molecular weight of the molecule is ≤15 kDa, preferably ≤10 kDa
c) determining at least the development of the transcutaneous fluorescence (TF) for the test subject, and
d) determining from the development of the TF determined in step c) the glomerular filtration rate and the degree of renal injury that has been induced in the test subject.

While a fluorescent molecule according to the second aspect cannot cross the GFB in a healthy subject, this is different for the fluorescent molecule according to the third aspect. Molecules with a molecular weight ≤15 kDa can cross a fully functional glomerular filtration barrier. With a molecular weight ≤15 kDa, preferably ≤10 kDa the fluorescent molecule can pass and is readily excreted by the kidney. The decay in TF is therefore a direct measure for the GFR. The GFR however can be altered when renal injury occurs, for example where mechanical or chemical damage has been induced. In consequence, there is an altered development of the TF (e.g. decay in TF) for the fluorescent molecule, which again can be used as a readout for renal injury. Thus, the method provides means to determine the degree and/or stage of loss of renal filtration rate as well as means to assess the renal glomerular filtration function. This readout system can be used independently or in combination with one or both readout systems according to the first and second aspect of the current invention. Different fluorophores might be used to distinguish between the readout for the second and third aspect.

The fluorescent molecule described for the third aspect of the current invention is a pharmaceutically suitable fluorescent molecule or a composition thereof. Preferably, the fluorescent molecule can cross a fully functional glomerular filtration barrier for the subject species at hand. In some preferred embodiments, the pharmaceutically suitable, fluorescent molecule has a molecular weight of ≤10 kDa or ≤15 kDa. In a preferred embodiment, the pharmaceutically suitable, fluorescent molecule has a(n) (average) molecular weight of approx. ≤1, ≤2, ≤3, ≤4, ≤5, ≤6, ≤7, ≤8, ≤9, ≤10, ≤11, ≤12, ≤13, ≤14 or ≤15 kDa, wherein in this particular context, the term approx. refers to +/−1 kDa. In some embodiments, said molecule comprises a polymer or a sugar. In some embodiments said molecule comprises sinestrin or inulin. In some embodiments said molecule comprises a Fluorescein isothiocyanate (FITC) or any other fluorescent dye suitable for detection. In a preferred embodiment the pharmaceutically suitable, fluorescent molecule comprises a polymer such as sinestrin and a fluorescent dye such as FITC.

Thus, except for the fluorescent molecule, all descriptions, embodiments, advantages and examples relating to the second aspect likewise apply for the third aspect. In particular, this holds true with respect to injury induction, administration schedule and administration method for the fluorescent molecule, as well as determination of the development of the TF. General schemes for experimental setups enabling the method according to the third aspect are given in example 9, as well as FIGS. 21 and 23. The GFR can be calculated based on the development of the TF as known in the art and as shown for example in FIGS. 22 and 24.

According to the current invention there is provided a renal injury model, wherein the renal injury model is created with a method according to aspect 1, 2 and/or 3.

The renal injury models according to the first, second and/or third aspect can be used for identifying, testing, characterizing or screening candidate molecules to treat renal injury. In some embodiments, the method according to any of the aspects is used to identify, test, characterize or screen candidate molecules to treat renal injury. In some embodiments, the method according to any of the aspects is used to identify, test, characterize or screen candidate molecules to induce or modulate renal injury.

According to a fourth aspect of the invention, there is provided a method of identifying, testing or characterizing a candidate molecule for its suitability to modulate or treat renal injury, wherein the method comprises the following steps:

a) inducing, in a test subject, renal injury by administering subcutaneously a bolus of a renal injury inducer, in a dosage sufficiently high to induce renal injury,
b) administering to the subject a candidate molecule,
c) determining at least the ACR in a urine sample taken from the subject, and
d) deducing, from the ACR determined in step c), whether or not the candidate molecule is capable of modulating, alleviating or preventing the renal injury induced in the test subject.

According to a fifth aspect of the invention, there is provided a method of identifying, testing or characterizing a candidate molecule for its suitability to modulate or treat renal injury, wherein the method comprises the following steps:
a) inducing, in a test subject, renal injury by administering subcutaneously and/or intravenously a bolus of a renal injury inducer, in a dosage sufficiently high to induce renal injury,
b) administering a pharmaceutically suitable fluorescent molecule to the test subject, wherein the total molecular weight of the molecule is ≥60 kDa,
c) administering to the subject a candidate molecule,
d) determining at least the development of the TF for the test subject, and
e) deducing, from the development of the TF determined in step d), whether or not the candidate molecule is capable of modulating, alleviating or preventing the renal injury induced in the test subject.

According to a sixth aspect of the invention, there is provided a method of identifying, testing or characterizing a candidate molecule for its suitability to modulate or treat renal injury, wherein the method comprises the following steps:
a) inducing, in a test subject, renal injury by administering subcutaneously and/or intravenously a bolus of a renal injury inducer, in a dosage sufficiently high to induce renal injury,
b) administering a pharmaceutically suitable fluorescent molecule to the test subject, wherein the total molecular weight of the molecule is ≤15 kDa, preferably ≤10 kDa,
c) administering to the subject a candidate molecule,
d) determining at least the development of the TF for the test subject, and
e) deducing, from the development of the TF determined in step d), whether or not the candidate molecule is capable of modulating, alleviating or preventing the renal injury induced in the test subject.

Thus, the inventors have identified methods, which, surprisingly, allow to study new drugs with the potential ability to improve kidney function in a short time frame. The AGISHA, the GFBI, and the GFR-based model have several advantages in comparison to the original method described by Rippe C et al., 2007:
i) different injuries are available in the models to simulate different disease modes (e.g. example 8)
ii) they are responding to the injury inducer in a dose dependent manner (e.g. FIGS. 1, 2),
iii) they are reversible (e.g. after 24 h, see FIGS. 3, 4) allowing for a higher throughput in drug discovery and not inherently terminal for the subject,
iv) they do not require complicated surgical procedures such as animal ureter and femoral vein catheterizations of the animal or tracheotomy surgical procedure,
v) they do not require long term anesthesia, and
vi) despite diverging readout parameters (ACR for AGISHA, TF for GFBI and GFR-based model), all readout parameters are detectable in a short time frame, e.g., after 2 or 4 hours.

The aspects 4, 5 and 6 inherit all embodiments from their respective parent method, i.e. according to aspects 1, 2 and 3.

A candidate molecule according to the current invention can be any compound or molecule or composition thereof. For example, the candidate molecule can be a small molecule or a biomolecule, such as a recombinant protein, an antibody or a fragment thereof. Preferably the candidate molecule is pharmaceutically acceptable. In some embodiments the candidate molecule alleviates or prevents the renal injury, as described for candidate molecules Losartan and Enalapril. In some embodiments the candidate molecule is an inducer of renal injury and/or aggravates renal injury. As shown for Tivozanib in example 2, the invention also provides means to identify compounds lacking activity in treatment of renal injury. Examples 1 to 7 as well as the schemes shown in the respective figures describe the use of different AGISHA (FIGS. 1, 5, 9, 11), GFBI (FIGS. 13, 19) and GFR-based (FIGS. 21, 23) test model setups to test various candidate molecules for their impact on renal injury. A fast and efficient option to characterize and evaluate drugs for their potential to acutely modulate the GFR in a fast and reproducible manner is described in example 9.

The candidate molecule can be administered by any suitable method known in the art. For example, the administration of the candidate molecule can occur as described in example 1. In some embodiments the one or more candidate molecules are administered to the test subject intravenously, subcutaneously, intraperitoneally or per oral application (e.g. oral gavage).

In some embodiments the candidate molecule is administered before, simultaneously with or after administering at least a part of the fluorescent molecule. In some embodiments the candidate molecule is administered before, simultaneously with or after administering at least a part of the renal injury inducer. For instance, the candidate molecule can be administered approx. 180, 120, 60, 30 or 15 minutes prior to administering at least a part of the renal injury inducer. According to some embodiments, the candidate drug is given between ≤2 hrs and ≥30 minutes before administration of the first bolus of a renal injury inducer. Hence, according to the current invention, an experiment which provides information about the potential or characteristics of a candidate drug can for example last between 8 hrs and 2½ hrs.

According to the aspects at hand, the readout such as ACR, development of TF (e.g. decay of TF, or half-life of the fluorescent dye Ficoll-FITC in the peripheral blood compartment) obtained for an experimental group of subjects where a candidate molecule has been administered is compared to the readout obtained for a control group of subjects. Such a control group can be formed as known in the art. For example in some embodiments, the subjects of the control group are treated with a placebo, a vehicle control or a positive control, such as a molecule suitable for the treatment of renal injury. For instance, if administration of a candidate molecule leads to significantly less renal injury than a placebo or a vehicle control (as indicated by the respective readout ACR or development of TF), the candidate molecule is considered to be suitable for the treatment of renal injury. For instance, if administration of a candidate molecule leads to the same or significantly less renal injury than a positive control, the candidate molecule is considered to be suitable for the treatment of renal injury.

According to a seventh aspect of the invention, there is provided a method for screening a population of candidate molecules for their suitability to treat renal injury, wherein the method comprises the following steps:
- a) inducing, in at least two test subjects, renal injury by administering subcutaneously a bolus of a renal injury inducer, in a dosage sufficiently high to induce renal injury,
- b) administering to the test subjects molecules from a library of candidate molecules,
- c) determining at least the ACR in urine samples taken from the subjects, and
- d) deducing, from the ACR determined in step c), whether or not the molecules are capable of modulating, alleviating or preventing the renal injury induced in the test subjects.

According to an eighth aspect of the invention, there is provided a method for screening a population of candidate molecules for their suitability to treat renal injury, wherein the method comprises the following steps:
- a) inducing, in at least two test subjects, renal injury by administering subcutaneously and/or intravenously a bolus of a renal injury inducer, in a dosage sufficiently high to induce renal injury,
- b) administering a pharmaceutically suitable fluorescent molecule to the test subjects, wherein the total molecular weight of the molecule is ≤15 kDa or ≥60 kDa,
- c) administering to the test subjects molecules from a library of candidate molecules,
- d) determining at least the development of the TF for the test subjects, and
- e) deducing, from the development of the TF determined in step d), whether or not the molecules are capable of modulating, alleviating or preventing the renal injury induced in the test subjects.

The term "population" of candidate molecules, as used herein, refers to a multitude of candidate molecules, i.e., a collection of two or more candidate molecules. This population can be derived from a library of molecules, or can be synthesized on demand.

Surprisingly, the renal injury model according to the described aspects of the invention has a high physiological recovery rate, usually within 24 hours, as shown for instance in FIGS. 3, 4. This allows to perform multiple experiments of this setting in the same batch of animals, but with different concentrations of the same candidate molecule, with different administration modalities, or with different candidate molecules per se. In some cases a loss of sensibility towards the injury inducer may occur after a couple of repetitions. To minimize this effect, the recovery time of the animals between two experiments can then be set to more than 24 hours, e.g., 48 or 72 hours.

According to some embodiments, the readout (e.g. ACR or the development of the TF) determined in one or more test subjects is compared to the respective readout of one or more control subjects in which renal injury has been induced in the same way, but (i) without administration of a candidate molecule for the treatment of renal injury, or (ii) with administration of a placebo instead, or (iii) with administration of a positive control, such as a molecule suitable for the treatment of renal injury.

In some further embodiments of the invention, the readout determined in one or more test subjects is also compared to the readout of one or more control subjects in which renal injury has not been induced, e.g., because the bolus administered comprised only saline.

According to a ninth aspect of the invention there is provided a method for producing a composition for the treatment of renal injury, wherein the method comprises:
- a) manufacturing (i.e. producing) or providing a population of candidate molecules,
- b) screening said population of candidate molecules with a method according to any of the methods described before,
- c) determining a candidate molecule that has a strong or moderate alleviating or preventing effect on renal injury, and
- d) manufacturing (i.e. producing) a composition comprising said candidate molecule determined in step c) and at least one further pharmaceutically acceptable ingredient.

According to a tenth aspect of the invention, there is provided a molecule for the treatment of renal injury, wherein the molecule is identified with a method according to the specification disclosed herein.

According to the aforementioned aspect of providing with molecules for the treatment of renal injury, preferred molecules for the treatment of renal injury are selected from the list consisting of Enalapril, Losartan, an Heparanase (HPSE) inhibitor, preferably OGT2115, 4-({(4-carboxybutyl)[2-(5-fluoro-2-{[4'-(trifluoromethyl)biphenyl-4-yl]methoxy}phenyl)ethyl]amino}methyl)benzoic acid, and 5-cyclopropyl-2-[1-(2-fluorobenzyl)-1H-pyrazolo[3,4-b]pyridin-3-yl]pyrimidin-4-amine Both, 4-({4-carboxybutyl)[2-(5-fluoro-2-{[4'-(trifluoromethyl)biphenyl-4-yl]methoxy}phenyl)ethyl]amino}methyl)benzoic acid and 5-cyclopropyl-2-[1-(2-fluorobenzyl)-1H-pyrazolo[3,4-b]pyridin-3-yl]pyrimidin-4-amine are modulators of the soluble guanylate Cyclase (sGC). While 4-({(4-carboxybutyl)[2-(5-fluoro-2-{[4'-(trifluoromethyl)biphenyl-4-yl]methoxy}phenyl)ethyl]amino}methyl)benzoic acid modulates the soluble guanylate Cyclase (sGC) by activing it and thus is considered to be an sGC activator, 5-cyclopropyl-2[1-(2-fluorobenzyl)-1H-pyrazolo[3,4-b]pyridin-3-yl]pyrimidin-4-amine modulates the soluble guanylate Cyclase (sGC) by stimulating it and thus is considered to be a sGC stimulator. sGC is usually activated by (NO) and produces cGMP, which activates cGMP-dependent protein kinases (PKG) and is hydrolyzed by specific phosphodiesterases (PDE). 4-({(4-carboxybutyl)[2-(5-fluoro-2-{[4'-(trifluoromethyl)biphenyl-4-yl]methoxy}phenyl)ethyl]amino}methyl)benzoic is considered to activate sGC in analogy thereto, while 5-cyclopropyl-2-[1-(2-fluorobenzyl)-1H-pyrazolo[3,4-b]pyridin-3-yl]pyrimidin-4-amine is an NO-independent but heme-dependent sGC stimulator. Other than NO-dependent activators, 5-cyclopropyl-2-[1-(2-fluorobenzyl)-1H-pyrazolo[3,4-b]pyridin-3-yl]pyrimidin-4-amine ameliorates angiotensin II-induced cardiovascular remodeling in a rat model of hypertension (Hoffmann L S et al., (2015) PLoS ONE 10 (12): e0145048). It has been suggested that the effects on the extracellular matrix are exerted partially via cGMP, independently of blood pressure (Masuyama H et al., Hypertension 2006; 48: 972-978). Other examples of the positive effects of the sGC activator and stimulator have been reported by Stasch J P et al., Current Opinion in pharmacology, 2015. The vasodilatory and cytoprotective capacity of cGMP-axis activation results in a therapeutic strategy for several pathologies connected with glomerular injury (such as glomerulonephrithis, Peters H et al., Kidney International, 2004; 66: 2224-2236). The model according to the present invention is thereby capable of identifying molecules for the treatment of renal injury independent of the mode of action of the respective molecule.

According to an eleventh aspect of the invention, there is provided a molecule for the induction of renal injury, wherein the molecule is identified with a method according to the specification disclosed herein.

According to another aspect of the invention, there is provided a pharmaceutical composition for the treatment of renal injury, wherein the composition is produced with a method according to the specification disclosed herein. Particularly, compositions according to the present invention are provided on the basis of molecules that have been identified and provided by the aspects of the invention referred to herein.

EXAMPLES

The following description of the respective examples and figures, shows, in an exemplary fashion, preferred embodiments of the present invention. However, these drawings should by no means be understood as to limit the scope of the invention.

Example 1 AGISHA Model with AngII as Injury Inducer

Five groups with 10-12 mice per group (C57Bl/6, Charles River Laboratories, 6-7 weeks old) were set for one experiment. After delivery, animals remained in a temperature- and light-controlled room with standardized mouse chow and water ad libitum for a one week acclimatization period, following guidelines of local governmental institutions (LANUV Germany). The groups were divided as follows (see FIG. 1):
  1. Control group without AngII bolus injection, but with control saline and additional (oral) administration of drug vehicle (10% ethanol, 40% solutol, 50% water or saline).
  2. AngII group, treated with AngII in normal saline, and drug vehicle. AngII administration occurred in two bolus injections (i.v.+s.c.) of 10 µg (5 µg i.v.+5 µg s.c.), 16 µg (8 µg i.v.+8 µg s.c.) and 20 µg (10 µg i.v.+10 µg s.c.) per mouse, where the first bolus was injected intravenously and the second bolus subcutaneously. The drug vehicle was administered orally.
  3. Candidate groups 3 and 4: AngII injection and additional treatment with the investigated drug/drugs. For substance testing, drugs or appropriated vehicles were administered orally, via i.v., s.c., or i.p. Administration occurred prior to or after AngII-injection. For example, investigated drug/drugs were given orally 30 minutes before the induction of the injury.
  4. Group 5 is the positive control group Animals were injected with AngII and treated orally with Losartan 30 mg/kg. Losartan is an AngII receptor blocker $AT_1$ (Pieter B M et al, Pharma. Rev., 1993, Kang P M et al, Progress in Cardiology, 1994). AngII bolus had no effect on ACR at the end of the experiment.

After AngII injection animals were placed in metabolic cages (Technoplast, Italy) for urine collection for up to 4 hours. At the end of the experiment the urine was analyzed to quantify the ACR. More specifically, the collected urine was analyzed using an automatic analyzer for urinary albumin as well as urinary creatinine (Coban® Integra 400, Roche, Basel, SUI) or using the Mouse albumin ELISA kit (ABCAM, Cambridge, UK). During the development of the model it was surprisingly found, that the AngII-related glomerular damage is an acute-reversible injury that can be physiologically recovered by the animals (FIGS. 2-4). The AGISHA model was performed in 3 identical cycles with a one-week break for recovery.

Example 2 AGISHA Model with Vasopressin as Injury Inducer

Figure 7:
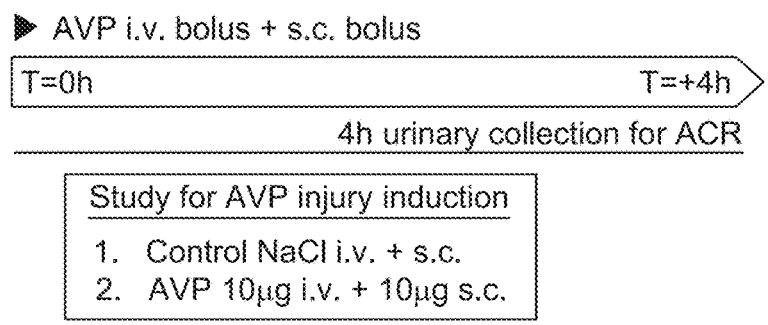
FIG. 7. Exemplary scheme of a Vasopressin arginine salt ("AVP") induced AGISHA model setup.

Example 2 was carried out as described for example 1 but with Vasopressin arginine salt ("AVP") as an inducer of ACR in the AGISHA model. A total dose of 20 µg/mouse AVP (10 µg i.v.+10 µg s.c.), as well as the administration route of combined intravenous and subcutaneous bolus injections was used to induce GBM injury (FIGS. 7-8).

Example 3 AGISHA Model with Candidate Molecules Enalapril, Losartan and Tivozanib Negative and positive control experiment. To confirm the findings shown in FIG. 2-4, the mode of action in AGISHA was investigated. In the following experiment, three of the animal groups were pre-treated with three different drugs by oral application 30 minutes before administration of injury inducer (see FIG. 5).
  1) Enalapril 10 mg/kg, an angiotensin-converting enzyme (ACE) inhibitor, is standard of care for high blood pressure. It was used as positive modulator control 1 of the renin-angiotensin system (RAS) in the AGISHA model.
  2) Losartan potassium, 30 mg/kg, angiotensin II type I receptor ($AT_1$) antagonist, standard of care for high blood pressure (Kang et al, 1994; Sica D A et al, Clin Parmacokinet., 2005) was used as positive modulator control 2 of the RAS system in the AGISHA model.
  3) Tivozanib, 3 mg/kg, vascular endothelial grow factor receptor tyrosine kinase inhibitor (Campas C et al, Drugs Fut., 2009) was used as negative modulator of the RAS system during AGISHA model.

Figure 6:
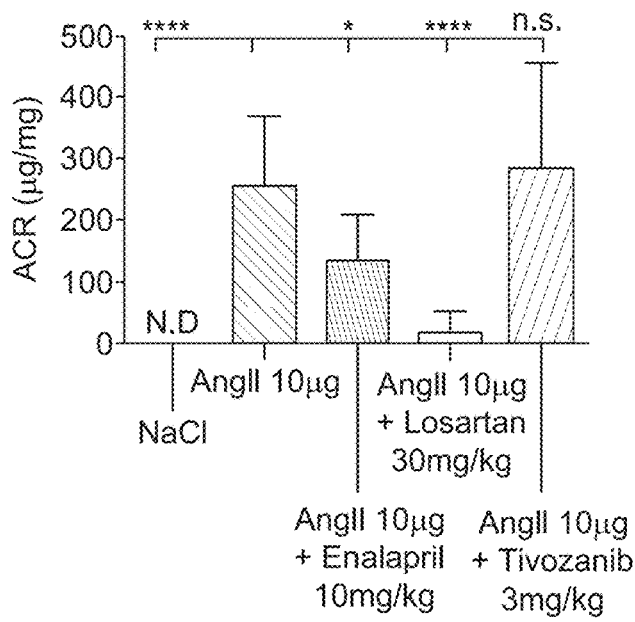

Experimental results are shown in FIG. 6. The injury caused by AngII is significantly reduced with the positive control Enalapril. The strongest effect is again obtained with the specific receptor $AT_1$ antagonist Losartan potassium. In contrast to that, the negative modulator Tivozanib shows no effect. The experiments clearly show that the assay according to the invention is suitable to reliably and reproducibly identify, and characterize, candidate molecules for the treatment of renal injury.

Example 4 AGISHA Model with Candidate Molecule OGT2115

To confirm the findings and to demonstrate the use of AGISHA model to evaluate possible anti-albuminuric compounds, the impact of OGT2115 (Tocris Bioscience, Bristol, UK) during acute glomerular injury was investigated (FIG. 9-10). McKenzie et al. (British Journal of Pharmacology 151, 1-14, 2007) reviewed the possibility to use the Heparanase (HPSE) inhibitor OGT 2115 in drug discovery against cancer and inflammation.

Diabetic nephropathy (DN) is the major life-threatening complication of diabetes. Abnormal permselectivity of the glomerular filtration barrier plays an important role in DN pathogenesis. Gil et al (Diabetes, 61(1), 2012, p. 208-16) showed in a heparanase-null (Hpse-KO) mouse streptozotocin (STZ)-induced diabetes model that deletion of the heparanase gene protects diabetic mice from DN. Furthermore, in the same study the authors showed the capability of the specific HPSE inhibitor to decrease the extent of ACR and renal damage in wild-type mouse models of DN.

In the following experiment, the animal groups are pre-treated with the HPSE inhibitor OGT2115 and the positive control Losartan potassium (see FIGS. 9-10).
1) OGT 2115, 40 mg/kg orally, specific HPSE inhibitor.
2) Losartan Potassium, 30 mg/kg orally, was used as positive control as described above.

Experimental results are shown in FIG. 10. The injury caused by AngII is significantly reduced with the HPSE inhibitor. Again, the experiments clearly show that the assay according to the invention is suitable to reliably and reproducibly identify and characterize candidate molecules for the treatment of glomerular injury.

Example 5 AGISHA Model with sGC Activator Candidate Molecule

Using the AGISHA model system as outlined in the examples before, urine was collected for four hours from wildtype C57/Bl6/J mice that had received two simultaneous injections of angiotensin II (AngII, 10 µg i.v.+10 µg s.c.). Albuminuria was measured as albumin-creatinine ratio (ACR) with Roche Cobas 1400. Group sizes ranged from 5-9 mice. All treatments were given orally prior to AngII injection.

Figure 12:
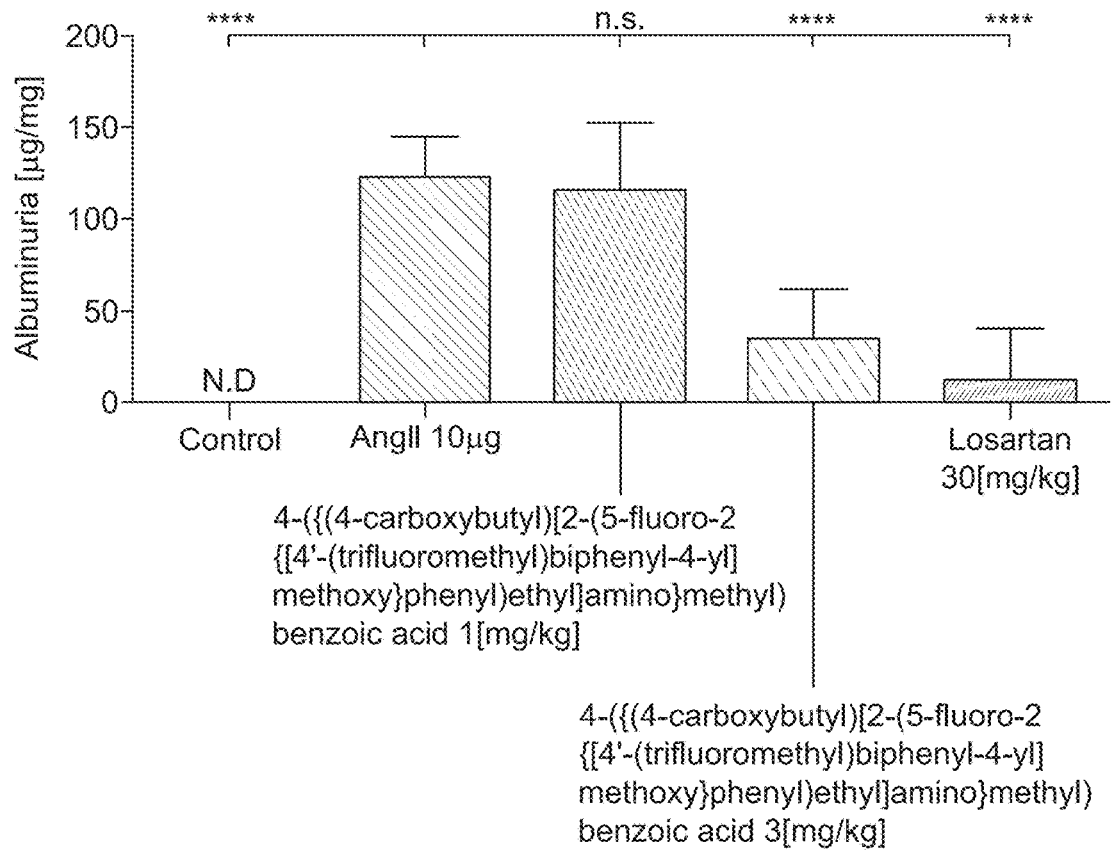
FIG. 12. sGC modulators reduce ACR in AGISHA model. Results from experimental setup according to FIG. 11. With a mean of 35±26 µg/mg, AngII induced ACR was significantly reduced for animals treated with sGC activator 4-({(4-carboxybutyl)[2-(5-fluoro-2-{[4'-(trifluoromethyl)biphenyl-4-yl]methoxy}phenyl)ethyl]amino}methyl)benzoic acid at a dose of 3 mg/kg. Losartan treated animals showed a highly significant reduction of AngII induced ACR by around 90%, N.D=no detectable ACR, mean±SD*//*/****=significant with p≤0.05/0.01/0.001/0.0001 vs. AngII (One-way ANOVA followed by Dunnett's Multiple Comparison post-hoc analysis).

Treatment was performed with 1 mg/kg or 3 mg/kg of sGC activator 4-({(4-carboxybutyl)[2-(5-fluoro-2-{[4'-(trifluoromethyl)biphenyl-4-yl]methoxy}phenyl)ethyl]amino}methyl)benzoic acid respectively. Treatment with 3 mg/kg of the compound reduced the ACR by 71% compared with the control group (FIG. 11-12). Losartan (30 mg/kg) was used as positive control.

Example 6 AGISHA Model with sGC Stimulator Candidate Molecule

Figure 13:
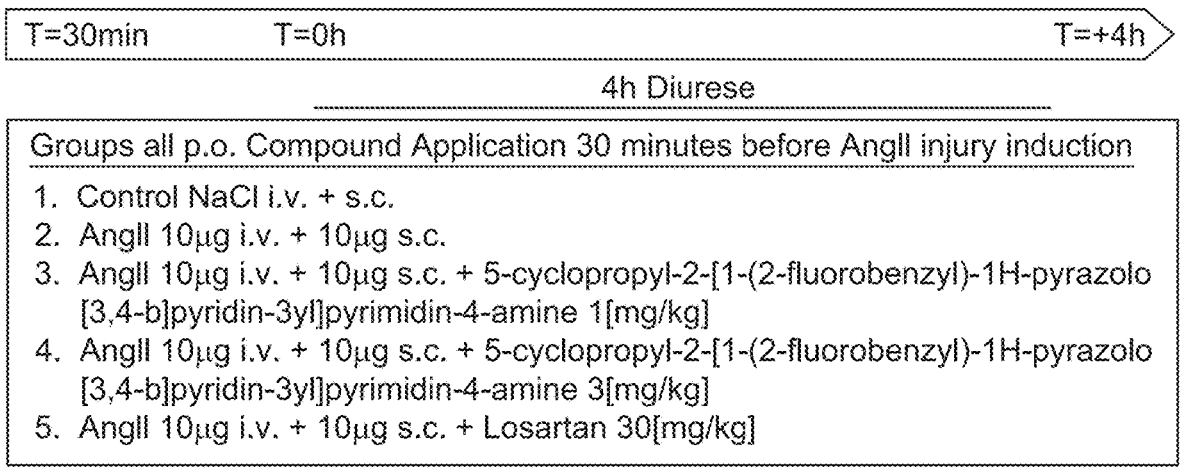
FIG. 13. Scheme of AGISHA experimental setup with sGC stimulator candidate molecule 5-cyclopropyl-2-[1-(2-fluorobenzyl)-1H-pyrazolo[3,4-b]pyridin-3-yl]pyrimidin-4-amine.
Figure 14:
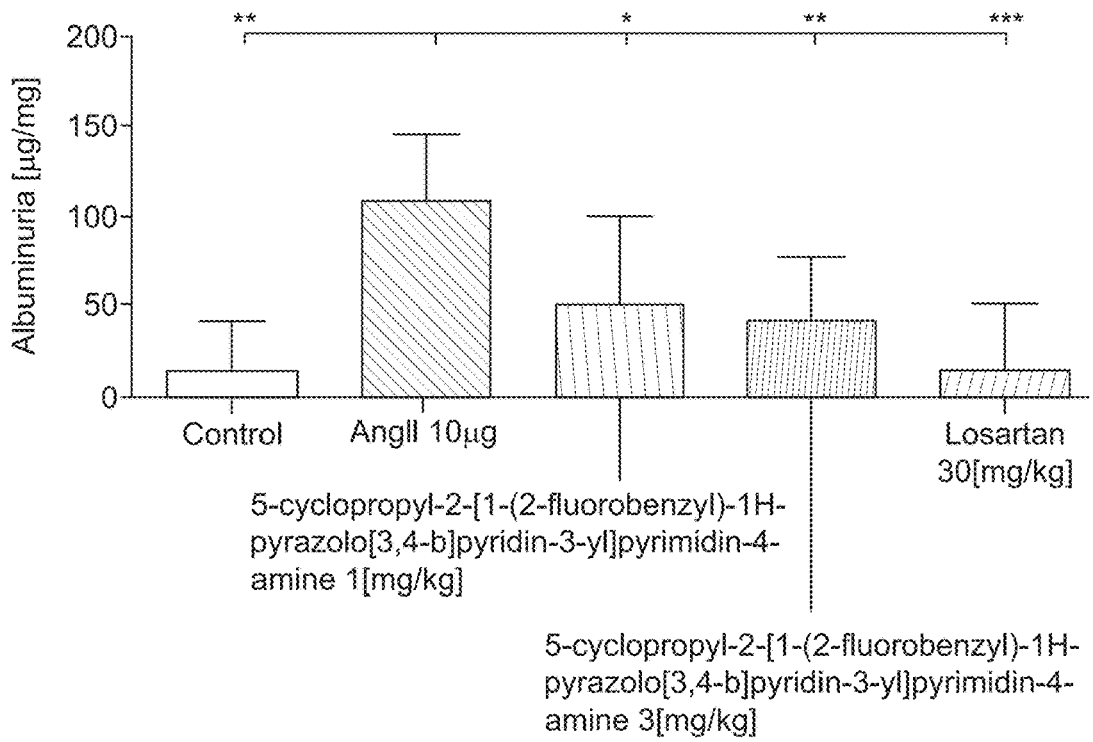
FIG. 14. sGC stimulators reduce ACR in AGISHA model. Results from experimental setup according to FIG. 13. Treatment with the sGC stimulator 5-cyclopropyl-2-[1-(2-fluorobenzyl)-1H-pyrazolo[3,4-b]pyridin-3-yl]pyrimidin-4-amine significantly reduced induction of ACR to a mean of 50±49 µg/mg and 42±35 µg/mg for the respective doses of 1 and 3 mg/kg. Losartan treated animals showed a highly significant reduction of AngII induced ACR by around 90%, N.D=no detectable ACR, mean±SD*//*/****=significant with p≤0.05/0.01/0.001/0.0001 vs. AngII (One-way ANOVA followed by Dunnett's Multiple Comparison post-hoc analysis).

The experiment was performed as described in example 5, except that the sGC stimulator 5-cyclopropyl-2-[1-(2-fluorobenzyl)-1H-pyrazolo[3,4-b]pyridin-3-yl]pyrimidin-4-amine was used for treatment. This compound reduced ACR significantly by 54% and 62% at 1 mg/kg and 3 mg/kg respectively (FIG. 13-14). Losartan (30 mg/kg) was used as positive control.

Example 7 Glomerular Filtration Barrier Integrity Test Model (GFBI Test)

After delivery, C57Bl/6/J male mice remained in a temperature- and light-controlled room with standardized mouse chow and water ad libitum for a one week acclimatization period, following guidelines of local governmental institutions (LANUV Germany). C57Bl/6/J mice (6-7 weeks) received an intravenous mixture of FITC-FICOLL 70 kDa (Sigma) and 10 µg AngII mix 100 µL, followed by a 10 µg (100 µL) subcutaneous AngII bolus as described in example 1. The groups were divided as follows, see FIG. 17:
1. Control group without AngII bolus injection, but with control saline 0.9%+Ficoll-FITC 150 mg/kg and additional s c administration of a bolus of NaCl 0.9%.
2. AngII group, treated with AngII in two bolus injections (10 µg/mouse of AngII+Ficoll-FITC, 150 mg/kg, both dissolved in 0.9% NaCl, first bolus injected i.v. via tail vein (5 µg AngII) and a second subcutaneous bolus injection (5 µg AngII).
3. AngII group, treated with AngII in two bolus injections (20 µg/mouse total AngII+Ficoll-FITC, 150 mg/kg 150 mg/kg, both dissolved in 0.9% NaCl, first bolus injected i.v. via tail vein (10 µg AngII) and a second subcutaneous bolus injection (10 µg AngII).

TF of the FICOLL-FITC was detected via the transcutaneous method developed by MediBeacon Inc. (MediBeacon Inc., Mo., USA). In brief: all experimental animals were shaved with standard mask anesthesia 1 h before the determination of TF for the FICOLL-FITC Immediately after the injury induction the portable transcutaneous measurement device was placed on the left dorsal back side of the animal for 2 hours. The results were analyzed with the MediBeacon Inc. software. FIG. 16 (A) shows a representative curve of the development of the transcutaneous fluorescence (TF) in the control group treated with 0.9% NaCl. The decay of the Ficoll-FITC dye was visualized as a flat line, with a half-life of ca. 396 minutes. FIG. 16 (B) shows a representative curve of the development of the transcutaneous fluorescence (TF) in animals treated with AngII. Fluorescent FICOLL-FITC is leaking through the injured GBM indicated by a sloping curve with a half-life of ca. 180 min. The half-life of the FICOLL-FITC fluorescence in healthy and injured mice is shown in FIG. 17.

Example 8 Sema3a as Non-Hypertensive Trigger to Study Non-Hypertensive Kidney Pathologies AngII induced GBM damage is a fast and stable trigger method to mimic human hypertensive glomerular disease or its complications. However, a non-hypertensive trigger was required to study the non-hypertensive kidney pathologies. Tapia R et al, KI, 2008 describe a robust, transient ACR within 4-24 h after injection of recombinant Sema3a. For the example at hand, other than described by Tapia R et al, Sema3a was injected i.v. and ACR and GFB integrity were evaluated in the following setup with the following experimental groups.
1) Male BL6/J mice were injected via tail vein with a mix of Ficoll-FITC 150 mg/kg and BSA (0.5 µg/g of BW), in a maximal volume of 100 µl.
2) Male BL6/J mice were injected via tail vein with a mix of Ficoll-FITC 150 mg/kg and Sema3a (R&D System, USA), 0.5 µg/g of BW, in a maximal volume of 100 µl.

Figure 19:
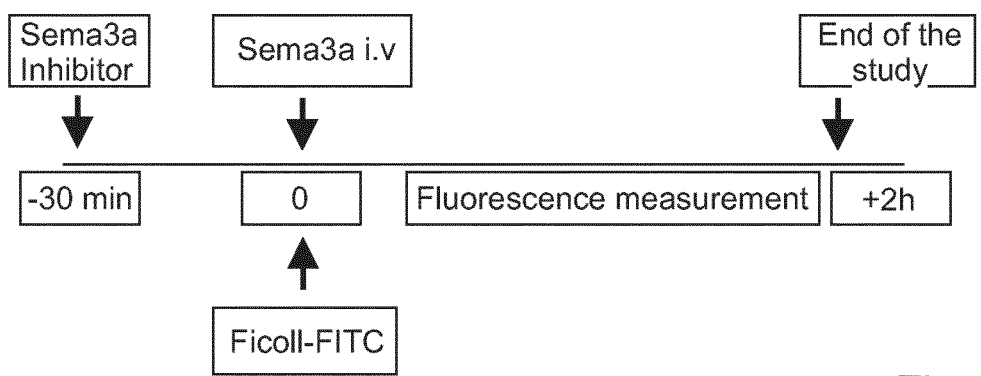
FIG. 19. Scheme of GFBI test model setup with Sema3a as injury inducer and Sema3a inhibitor as candidate molecule to study loss of GBM integrity.

The animals went under transcutaneous fluorescent measurement for 2 h, as described before. The GFB integrity test was able to detect the loss of fluorescent dye due to podocyte effacement as well as the increased ACR in the urine. As previously shown for the blood pressure dependent AngII-induced injury, these results demonstrate the possibility to use a blood pressure independent injury such as Sema3A in the GFBI test model to induce GBM injury. In order to confirm these findings and to demonstrate the suitability of the GFBI test model as a drug discovery screening method, model subjects were pre-treated with a Sema3a inhibitory peptide (Williams et al, Journal of Neurochemistry, 92(5), p. 1180-1190, 2005). This peptide is able to disrupt the ability of the Sema3A to induce the decay of the fluorescent dye. The experimental setup is shown in FIG. 19. The sensitivity of the GFBI test was evaluated as follows and subjects were pre-treated according to the following groups:
1. Control w/o injury induction (Control): Male C57 BL6/J mice were injected i.v. with peptide vehicle control (PBS), 30 min before i.v. injection of a mix of Ficoll-FITC 150 mg/kg and BSA, 0.5 µg/g of BW, in a maximal volume of 100 µl.

2. Injury control (Placebo): Male C57 BL6/J mice were injected i.v. with peptide vehicle control (PBS), 30 min before injection of a mix of Ficoll-FITC 150 mg/kg and Sema3a as 0.5 µg/g of BW, in a maximal volume of 100 µl.
3. Inhibitor: Male BL6/J mice were injected i.v. with 2.5 mg/kg of inhibitory peptide in PBS, 30 min before Sema3a/Ficoll-FITC 150 mg/kg injection.

Results are shown in FIG. 20. GBM integrity was significantly decreased in the injury control group compared with the control group w/o injury inducer. As expected the inhibitory peptide was able to restore the GBM integrity disruption caused by Sema3A.

Example 9 GFR Acute Modulation

Acute GFR modulation is a relevant phenomenon in the field of nephrology (Fergusan and Waikar, Clin. Chem., 58(4), 2012, p. 680-689). GFR is the major readout parameter for chronic kidney disease (CKD) stage assessment (Lopez-Giacoman and Madero, World J Nephrol. 4(1), 2015, 57-73). The GFR is also a very stable and robust physiological parameter that is subject to positive and negative feedback regulation. The following protocol and experimental setup (FIG. 21) was established to model acute GFR modulation.

Figure 22:
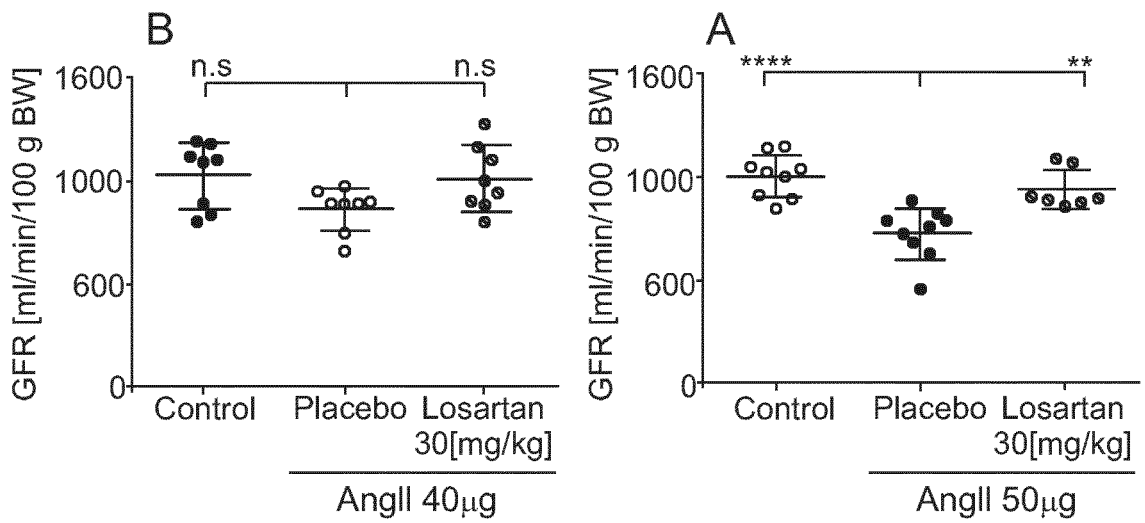
FIG. 22. GFR acute modulation depends on the AngII dose and can be reversed by administration of a positive RAS modulator. Results from experimental setup according to FIG. 21. The left graph (A) shows a decrease in GFR 2 hrs after bolus injection of 40 µg AngII. The GFR ratio was significantly reduced in the experimental setting where 50 µg AngII injury inducer where applied. Losartan (30 mg/kg) pre-treated animals showed a significant recovery of AngII induced loss of GFR, almost comparable with the NaCl control group. Mean±SD*//*/****=significant with p≤0.05/0.01/0.001/0.0001 vs. AngII (7-10 animals) (One-way ANOVA followed by Dunnett's Multiple Comparison post-hoc analysis).
Figure 23:
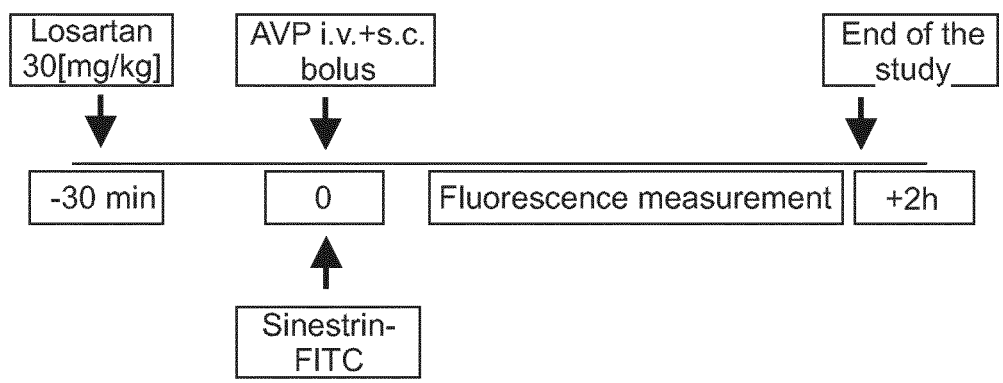
FIG. 23. Scheme of GFR-based model with injury inducer AVP, sinestrin-FITC, and pre-treatment with candidate compound Losartan (30 mg/kg).

Experiment A With Results Shown in FIG. 22 (A)
1. Control group without AngII bolus injection, but with control saline (0.9%)+Sinestrin-FITC 150 mg/kg and additional s c administration of 0.9% NaCl (100 µl+100 µl)
2. AngII group, treated with AngII in two bolus injections: First bolus of 20 µg/mouse of AngII in normal saline administered in combination with Sinestrin-FITC 150 mg/kg, 50 µl+50 µl, injected via tail vein. Second bolus injected s.c. comprising 20 µg AngII, 100 µl.
3. Losartan group was treated orally with 30 mg/kg of Losartan Potassium, 30 min prior to the AngII injury. AngII injury occurred in two bolus injections as described for the AngII group (total 40 µg).

The Losartan is an AngII receptor blocker. Indeed the AngII bolus had no effect on the GFR at the end of the experiment.

Experiment B With Results Shown in FIG. 22 (B)
1. Control group without AngII bolus injection, but with control saline (0.9%)+Sinestrin-FITC 150 mg/kg and additional s.c. administration of 0.9% NaCl (100 µl+100 µl)
2. AngII group, treated with AngII in two bolus injections: First bolus of 20 µg/mouse of AngII in normal saline administered in combination with Sinestrin-FITC 150 mg/kg, 50 µl+50 µl, injected via tail vein. Second bolus injected s.c. comprising 30 µg AngII, 100 µl.
3. Losartan group was treated orally with 30 mg/kg of Losartan Potassium, 30 min prior to the AngII injury. AngII injury occurred in two bolus injections as described for the AngII group (total 50 µg).

Figure 21:
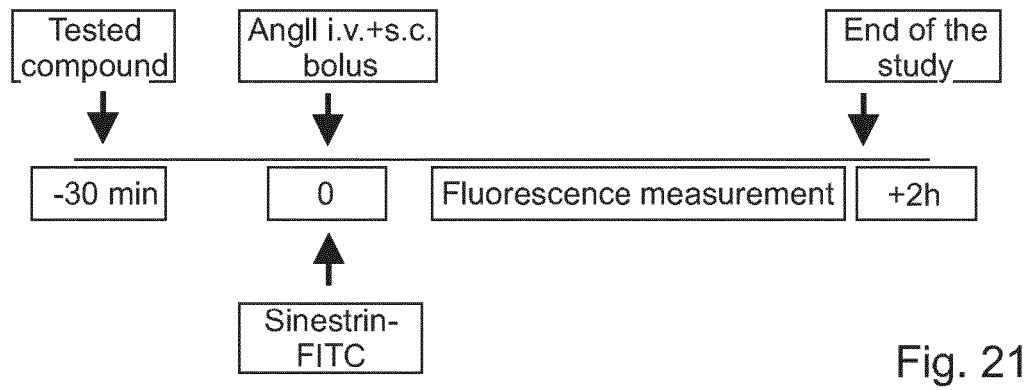
FIG. 21. Scheme of GFR-based model with injury inducer AngII, fluorescent molecule sinestrin-FITC, and pre-treatment with a candidate compound for the determination of the GFR.

For substance testing, animals were pre-treated with the respective drugs or vehicles 30 min before AngII-injection, via oral gavage, s.c, i.p., or tail vein injection. Subsequently, AngII/Sinestrin-FITC mix bolus was administered to the animals with the tracer (FIG. 21). The experimental readout, GFR, was decreased but not significantly decreased after bolus injection of a total of 40 µg AngII compared with the control group. The SoC Losartan was able to completely reverse the effect (FIG. 22 A). An increase of the s.c. dose of AngII of resulted in a highly significant reduction of the GFR compared with the control group (FIG. 22 B). In fact, Losartan treatment restored the GFR.

Figure 24:
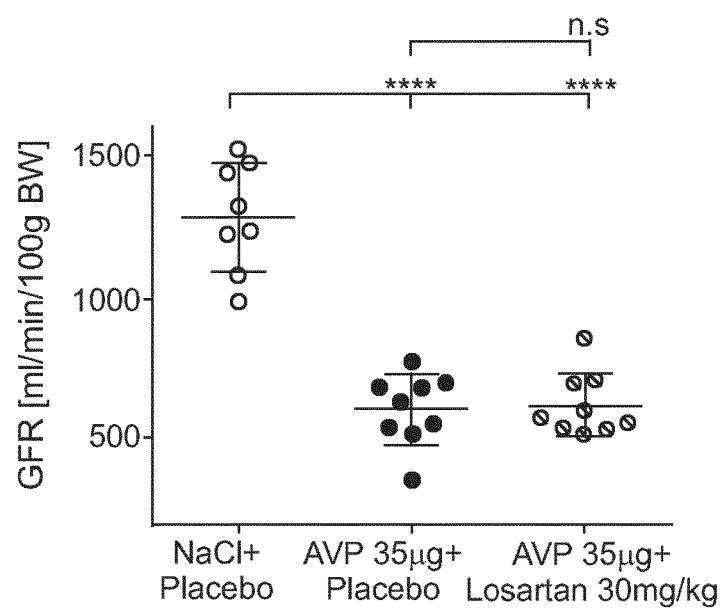
FIG. 24. Impact of pre-treatment with RAS inhibitor Losartan on GFR reduction induced by AVP. Results from experimental setup according to FIG. 23. The graph shows a significant decrease in GFR 2 hrs after AVP bolus injection (35 µg). Pre-treatment with Losartan did not restore or prevent the AVP induced loss of GFR, pointing towards a different mode of action than for AngII-based injury induction. Mean±SD*//*/****=significant with p≤0.05/0.01/ 0.001/0.0001 vs. NaCl+Placebo (8-10 animals) (One-way ANOVA followed by Dunnett's Multiple Comparison post-hoc analysis) or mean±SD*//*/****=significant with p≤0.05/0.01/0.001/0.0001, AVP+Placebo vs Losartan (8-10 animals) (unpaired T-test).

A similar setup (FIG. 23) was used with AVP (Sigma-Aldrich, Mo.) at a dose of 35 µg, i.e. using a first bolus with 15 µg AVP, injected i.v. in combination with Sinestrin-FITC 150 mg/kg (50 ul+50 ul) and using a second bolus of 20 µg AVP, 100 uL, injected i.v. As before GFR, was decreased by AVP compared with the control group. However, Losartan treatment did not restore the normal GFR (FIG. 24). These data suggest that AVP injury is driven by a different mode of action.

The invention claimed is:

1. A method for creating a renal injury model, wherein the method comprises the following steps:
a) inducing, in a test subject, renal injury by administering subcutaneously and/or intravenously a bolus of a renal injury inducer, in a dosage sufficiently high to induce renal injury,
b) determining at least the albumin creatinine ratio (ACR) in a urine sample taken from the test subject, and
c) determining from the ACR determined in step b) the degree of renal injury that has been induced in the test subject,
wherein the renal injury inducer is selected from the group consisting of angiotensin II, vasopressin, Sema3a and heparanase.

2. The method according to claim 1, wherein the test subjects are rodents.

3. The method according to claim 2, wherein the rodents are mice or rats.

4. The method according to claim 1, wherein the determination of the ACR is carried out between ≥2 hrs and ≤6 hrs after administration of the bolus of renal injury inducer.

5. A method of identifying, testing or characterizing a candidate molecule for its suitability to treat renal injury, wherein the method comprises the following steps:
a) inducing, in a test subject, renal injury by administering subcutaneously and/or intravenously a bolus of a renal injury inducer, in a dosage sufficiently high to induce renal injury,
b) administering to the subject a candidate molecule,
c) determining at least the ACR in a urine sample taken from the subject, and
d) deducing, from the ACR determined in step c), whether or not the candidate molecule is capable of treating the renal injury induced in the test subject,
wherein the renal injury inducer is selected from the group consisting of angiotensin II, vasopressin, Sema3a and heparanase.

6. The method according to claim 5, wherein one or more candidate molecules are administered to the test subject, and further wherein the one or more candidate molecules are administered intravenously, subcutaneously, intraperitoneally or per oral application.

7. A method for screening a population of candidate molecules for their suitability to treat renal injury, wherein the method comprises the following steps:
a) inducing, in at least two test subjects, renal injury by administering subcutaneously and/or intravenously a bolus of a renal injury inducer, in a dosage sufficiently high to induce renal injury,
b) administering to the test subjects molecules from a library of candidate molecules,
c) determining at least the ACR in urine samples taken from the subjects, and
d) deducing, from the ACR determined in step c), whether or not the molecules are capable of treating the renal injury induced in the test subjects, wherein the renal injury inducer is selected from the group consisting of angiotensin II, vasopressin, Sema3a and heparanase.

8. A method for creating a renal injury model, wherein the method comprises the following steps:
   a) inducing, in a test subject, renal injury by administering subcutaneously and/or intravenously a bolus of a first renal injury inducer, and a second bolus of the same or a different renal injury inducer, in a dosage sufficiently high to induce renal injury together with the bolus of the first renal injury inducer,
   b) determining at least the albumin creatinine ratio (ACR) in a urine sample taken from the test subject, and
   c) determining from the ACR determined in step b) the degree of renal injury that has been induced in the test subject,
   wherein the renal injury inducer is selected from the group consisting of angiotensin II, vasopressin, Sema3a and heparanase.

9. The method according to claim 8, wherein the two boli of injury inducer are administered simultaneously, or in sequence.

10. A method of identifying, testing or characterizing a candidate molecule for its suitability to treat renal injury, wherein the method comprises the following steps:
   a) inducing, in a test subject and in a control subject, renal injury by administering subcutaneously and/or intravenously a bolus of a renal injury inducer, in a dosage sufficiently high to induce renal injury, wherein the test subject and the control subject are administered the same renal injury inducer in the same dosage,
   b) administering to the test subject a candidate molecule,
   c) administering to the control subject (i) none of the candidate molecule, (ii) a placebo, and/or (iii) a positive control that is a molecule suitable for the treatment of renal injury,
   d) determining at least the ACR in a urine sample taken from the subject and the ACR in a urine sample taken from the control subject,
   e) comparing the ACR determined from the test subject and the control subject,
   f) deducing, from the ACR comparison in step e), whether or not the candidate molecule is capable of treating the renal injury induced in the test subject,
   wherein the renal injury inducer is selected from the group consisting of angiotensin II, vasopressin, Sema3a and heparanase.

* * * * *